(12) United States Patent
Coric et al.

(10) Patent No.: US 11,554,117 B2
(45) Date of Patent: *Jan. 17, 2023

(54) GLUTAMATE AGENTS IN THE TREATMENT OF MENTAL DISORDERS

(71) Applicant: YALE UNIVERSITY, New Haven, CT (US)

(72) Inventors: Vladimir Coric, Madison, CT (US); John H. Krystal, Woodbridge, CT (US); Gerard Sanacora, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/031,250

(22) Filed: Jul. 10, 2018

(65) Prior Publication Data
US 2018/0318288 A1 Nov. 8, 2018

Related U.S. Application Data

(60) Continuation of application No. 14/278,573, filed on May 15, 2014, now Pat. No. 10,052,318, which is a division of application No. 11/399,188, filed on Apr. 5, 2006, now Pat. No. 8,778,979.

(60) Provisional application No. 60/668,735, filed on Apr. 5, 2005, provisional application No. 60/669,774, filed on Apr. 7, 2005, provisional application No. 60/690,187, filed on Jun. 13, 2005, provisional application No. 60/694,621, filed on Jun. 27, 2005, provisional application No. 60/756,472, filed on Jan. 4, 2006.

(51) Int. Cl.
| | | |
|---|---|---|
| A61K 31/135 | (2006.01) | |
| A61K 31/425 | (2006.01) | |
| A61K 31/428 | (2006.01) | |
| A61K 31/485 | (2006.01) | |
| A61K 31/198 | (2006.01) | |
| A61K 31/43 | (2006.01) | |
| A61K 31/545 | (2006.01) | |
| A61K 45/06 | (2006.01) | |
| G02B 1/10 | (2015.01) | |
| G02B 5/28 | (2006.01) | |
| H01L 27/146 | (2006.01) | |
| A61K 31/13 | (2006.01) | |

(52) U.S. Cl.
CPC ............ *A61K 31/485* (2013.01); *A61K 31/13* (2013.01); *A61K 31/198* (2013.01); *A61K 31/425* (2013.01); *A61K 31/428* (2013.01); *A61K 31/43* (2013.01); *A61K 31/545* (2013.01); *A61K 45/06* (2013.01); *G02B 1/10* (2013.01); *G02B 5/281* (2013.01); *G02B 5/283* (2013.01); *G02B 5/285* (2013.01); *H01L 27/14621* (2013.01); *H01L 27/14685* (2013.01)

(58) Field of Classification Search
CPC .... A61K 31/425; A61K 31/13; A61K 31/198; A61K 31/428; A61K 31/43; A61K 31/485; A61K 31/545; A61K 45/06; A61P 25/00

See application file for complete search history.

(56) References Cited

U.S. PATENT DOCUMENTS

| | | | |
|---|---|---|---|
| 4,370,338 A * | 1/1983 | Mizoule ............... | C07D 277/82 514/367 |
| 4,812,481 A | 3/1989 | Reischig et al. | |
| 5,057,321 A | 10/1991 | Edgren et al. | |
| 5,190,763 A | 3/1993 | Edgren et al. | |
| 5,192,550 A | 3/1993 | Edgren et al. | |
| 5,221,536 A | 6/1993 | Edgren et al. | |
| 5,358,721 A | 10/1994 | Guittard et al. | |
| 5,866,585 A | 2/1999 | Fogel | |
| 5,952,389 A | 9/1999 | Fogel | |
| 6,057,373 A | 5/2000 | Fogel | |
| 6,217,905 B1 | 4/2001 | Edgren et al. | |
| 6,228,888 B1 | 5/2001 | Slusher | |
| 6,284,276 B1 | 9/2001 | Rudnic et al. | |
| 6,294,583 B1 | 9/2001 | Fogel | |
| 6,362,226 B2 | 3/2002 | Phillips, III et al. | |
| 6,387,956 B1 | 5/2002 | Shapira et al. | |
| 6,391,922 B1 | 5/2002 | Fogel | |

(Continued)

FOREIGN PATENT DOCUMENTS

| | | |
|---|---|---|
| EP | 0305276 A2 | 1/1989 |
| WO | 199108291 | 5/1991 |

(Continued)

OTHER PUBLICATIONS

U.S. Appl. No. 60/731,947, filed Oct. 31, 2005, published on May 17, 2007 as US 20070112017, pp. 1-40 (Year: 2007).*

(Continued)

*Primary Examiner* — Sarah Pihonak
(74) *Attorney, Agent, or Firm* — Henry D. Coleman; R. Neil Sudol

(57) ABSTRACT

Methods of treating mental disorders, including anxiety disorders such as obsessive-compulsive disorder, are provided. The methods comprise administering an effective amount of a glutamate modulator to an individual in need thereof. Also provided are methods of enhancing the activity of a serotonin reuptake inhibitor (SRI) comprising co-administering a glutamate modulator and a serotonin reuptake inhibitor. Pharmaceutical composition comprising a serotonin reuptake inhibitor and a glutamate modulator are also provided.

2 Claims, 13 Drawing Sheets

(56) References Cited

U.S. PATENT DOCUMENTS

| | | | |
|---|---|---|---|
| 6,566,401 | B2 | 5/2003 | Herzenberg et al. |
| 6,872,739 | B1* | 3/2005 | Polman ................ A61K 31/428 |
| | | | 514/367 |
| 2002/0013366 | A1 | 1/2002 | Fogel |
| 2002/0119912 | A1 | 8/2002 | Fogel |
| 2003/0162694 | A1 | 8/2003 | Meyerhoff |
| 2003/0180352 | A1* | 9/2003 | Patel ..................... A61K 9/1617 |
| | | | 424/465 |
| 2003/0195139 | A1 | 10/2003 | Corsi et al. |
| 2006/0062851 | A1 | 3/2006 | Vergez et al. |
| 2006/6063810 | | 3/2006 | Vergez et al. |
| 2006/0121488 | A1 | 6/2006 | Rothstein |
| 2006/0142398 | A1 | 6/2006 | Went |
| 2006/0159763 | A1 | 7/2006 | Meyer et al. |
| 2006/0167068 | A1 | 7/2006 | Feuerstein et al. |
| 2006/0270647 | A1 | 11/2006 | Coric et al. |
| 2007/0112017 | A1* | 5/2007 | Barlow ................. A61K 31/137 |
| | | | 514/282 |

FOREIGN PATENT DOCUMENTS

| | | |
|---|---|---|
| WO | 199205475 | 2/1992 |
| WO | 0056301 A2 | 9/2000 |
| WO | 200112184 | 2/2001 |
| WO | 2004056335 | 7/2004 |
| WO | 2004087116 | 10/2004 |
| WO | 2004100992 A2 | 11/2004 |
| WO | 2006089494 | 8/2006 |
| WO | 2006108055 | 10/2006 |
| WO | 2007043753 | 4/2007 |

OTHER PUBLICATIONS

Sheikh et al., Depression & Anxiety, vol. 18, pp. 187-197, publ. 2003 (Year: 2003).*

Jing Du, et al. Bipolar disorder: involvement of signaling cascades and AMPA receptor trafficking at synapses. Neuron Glia Biology, 2004;1(3):abstract.

CONN MP. Sourcebook of Models for Biomedical Research. 2008, Humana Press Inc. Totowa, New Jersey, USA.

Ryberg H, et al. A double-blind randomized clinical trial in amyotrophic lateral sclerosis using lamotrigine: effects on CSF glutamate, aspartate, branched-chain amino acid levels and clinical parameters. Acta Neurol Scand, 2003;108:1-8.

Spandoni F, et al. Lamotrigine derivatives and riluzole inhibit INa.P in cortical neurons. Neuropharmacology and Neurotoxicology, 2002;13(9):1167-1170.

Mestre M, et al. Frequency-independent blockade of cardica Na+ channels by riluzole: comparison with established anticonvulsants and class I anti-arhythmics. Fundam Clin Pharmacol, 2000;14:107-117.

Stefani A, et al. Differential Inhibition by Riluzole, Lamotrigine, and Phenytoin of Sodium and Calcium Currents in Cortical Neurons: Implications for Neuroprotective Strategies. Experimental Neurology, 1997;147:115-122.

Sasaki-Hamada S, et al. Riluzole Does Not Affect Hippocampal Synaptic Plasticity and Spatial Memory, Which are Impaired by Diazepam in Rats. J Pharmacol Sci, 2013;122:232-236.

Farach FJ, et al. Pharmacological treatment of anxiety disorders: Current treatments end future directions. Journal of Anxiety Disorders, 2012;26:833-843.

Mirza NR, et al. Lamotrigine has an anxiolytic-like profile in the rat conditioned emotional response test of anxiety: a potential role for sodium channels? Psychopharmacology, 2005;180:159-168.

Munro G, et al. Pharmacological comparison of anticonvulsant drugs in animal models of persistent pain and anxiety. Neuropharmacology, 2007;53:609-618.

Sugiyama A, et al. Riluzole produces distinct anxiolytic-like effects in rate without the adverse effects associated with benzodiazepines. Neuropharmacology, 2012;62:2489-2498.

Saitoh A, et al. The voltage-gated sodium channel activator veratrine Induces anxiogenio-like behaviors in rats, Behavioural Brain Research, 2015;292:316-322.

Kaluev AV, et al., Behavioral Effects of Penicillin in a Test for Anxiety in Rats. Bulletin of Experimental Biology and Medicine, 1995;120(10).

Zohar J, et al. Anxiety disorders: a review of ticyclic antidepressants and selective serotonin reuptake Inhibitors. Acta Psychiatr Scand, 2000;101:39-49.

Matthew, et al. Open-Label Trial of Riluzole in Generalized Anxiety Disorder. Am J Psychiatry. 2005;162:2379-2381.

Frizzo, et al. Riluzole Enhances Glutamate Uptake in Rat Astrocyte Cultures. Cellular and Molecular Neurobiology. 2004;24.

Goodman & Gilmans: The Pharmacological Basis of Therapeutics. Tenth Edition, 2001. pp. 450-451.

Hamilton Anxiety Scale, Encyclopedia of Mental Disorders. pp. 1-5. Accessed from the internet, first published on the internet in May 2006.

Gate, et al. Clinical Evidence: A Publication of BMJ Publishing Group. Generalized Anxiety Disorder, American Family Physician. 2003:p. 1-4.

Hamilton, M. The Assessment of Anxiety States by Rating. British Journal of Medical Psychology, 1959,32(1):50-55.

Kreischmer, et al. Riluzole, a glutamate release inhibitor, and motor behavior. Naunyn-Schmiedeberg's Arch Pharmacol, 1998;358:181-190.

Dennenberg VH. Open-Field Behavior in the Rat: What does it Mean? Ann NY Acad Sci, 1969:159(3).852-859.

Davidson JRT. First-Line Pharmacotherapy Approached for Generalized Anxiety Disorder. J Clin Psychiatry, 2009;70:25-31.

Brown RJ Jr. Amyotrophic lateral sclerosis—a new role for old drugs. N Engl J Med, 2005:352:1376-1378.

Rothstein JD, et al. Beta-lactam antibiotics offer neuroprotection by increasing glutamate transporter expression. Nature. 2005;433:73-77.

Mathew SJ, et al. Riluzole in Generalized Anxiety Disorder: An Open-Label Trial. Neuropsychopharacology, 2004;29:S154.

Krystal JH et al. Glutamate and GABA systems as targets for novel antidepressant and mood-stabilizing treatments. Mol Psychiatry. 2002;7:S71-S80.

Manji HK, et al. Molecular and cellular mechanisms underlying mood stabilization in bipolar disorder: implications for the development of improved therapeutics. Mol Psychiatry, 2002;7:S1-S7.

National Institutes of Health, Riluzole to Treat Depression in Bipolar Disorder. Feb. 6, 2003. Last Updated: Mar. 13, 2009.

Zarate CA, et al. Modulators of the glutamatergic system: implications for the development of improved therapeutics in mood disorders, Psychopharmacol Bull, 2002,36(4):35-83.

Brown and Phil. Amyotrophic Lateral Sclerosis—A New Role for Old Drugs. The New England Journal of Medicine, 200;352(13):30-33.

Coric, et al. Beneficial Effects of the Antiglutamatergic Agent Riluzole in a Patient Diagnosed with Obsessive-Compulsive Disorder and Major Depressive Disorder. Psychopharmacology, 2003;167:219-220.

Lafleur, et al. N-Acetylcystein Augmentation on Serotonin Reuptake Inhibitor Refractory Obsessive Compulsive Disorder. Psychopharmacology, 2006;184:254-256.

Sanacora, et al, Riluzole Augmentation for Treatment-Resistant Depression. Am J Psychiatry, 2004:161(11):2132.

Singh, et al. Case report: Successful riluzole augmentation therapy in treatment-resistant bipolar depression following the development of rash with lamotrigine. Psychopharmacology, 2004;173:227-228.

Zarate, et al. An open-label trial of the glutamate-modulating agent riluzole in combination with lithium for the treatment of bipolar depression. Biol Psychiatry, 2005;57(4):430-432.

Zarate, et al. An open-label trial of riluzole in patients with treatment-resistant major depression. Am J Psychiatry, 2004;161(1):171-174.

Berman, et al. Antidepressant Effects of Ketamine in Depressed Patients. Biol Psychiatry, 2000;47:351-354.

Goddard, et al. Serotoninergic Mechanisms in the Treat of Obessive-Compulsive Disorder, Drug Discover Today, 2008;13:325-332.

(56) References Cited

OTHER PUBLICATIONS

Greenberg and Meyers. Treatment of Major Depression and Parkinson's Disease With Combined Phenelzine and Amantadine. Am J Psychiatry, 1986:142:273-274.
Hovestadt, et al. Drug Treatment in Parkinson's Disease. J Drug Therapy Research, 1992;17(5):147-151.
Jehle, et al. Effects of Riluzole on Electrically Evoked Neurotransmitter Release, British J Pharmacology, 2000;130:1227-1234.
Krystal, et al. Therapeutic Implications of the Hyperglutamatergic Effects of NMDA Antagonists, Neuropsychopharmacology, 1999;21:N6.
Marek, et al. Physiological Antagonism Between 5-Hydroxytryptamine2A and Group II Metabotropic Glutamate Receptors in Profrontal Cortex. The Journal of Pharmacology and Experimental Therapeutics, 2000;292:76-87.
Rosenberg, et al. Decrease in Cudate Glutamatergic Concentrations in Pediatric Obsessive-Compulsive Disorder Patients Taking Paroxetine. J Am Acad Child Adolesc Psychiatry, 2000;39(9):1096-1103.
Stefani, et al. Differential Inhibition by Riluzole, Lamotrigine, and Phenytoin of Sodium and Calcium Currents in Cortical Neurons: Implications for Neuroprotective Strategies. Experimental Neurology, 1997;147:115-122.
Urbani and Belluzzi. Riluzole Inhibits the Persistent Sodium Current in Mammalian CNS Neurons. European Journal of Neuroscience, 2000;12:3567-3574.
Frizzo M, et al. Riluzole Enhances Glutamate Uptake in Rat Astrocyte Cultures. Cellular and Molecular Neurobiology, 2004;24:1:123-128.
Machado-Vieira R, et al. The Role of the Tripartite Glutamatergic Synapse in the Pathophysiology and Therapeutics of Mood Disorders. The Neuroscientist, 2009;15(5):525-539.
Nokke J. Riluzole. Lancet, 1996;348:795-799.
Stein DJ, et al. Pharmacotherapy for post traumatic stress disorder (PTSD). Cochrane Database of Systemic Reviews, 200. https://doi.org/10.1002/14651858.CD002795, 2000.
Ipser J, et al. Pharmacotherapy for post-traumatic stress disorder—a systemic review and meta-analysis. S Afr Med J, 2006;96(10):1088-1096.
Stein DJ, et al. Pharmacotherapy for post traumatic stress disorder (PTSD) (Review) Cochrane Database of Systemic Reviews, 2006;1:Art. No:CD002795, 2015.
Averill LA; et al. Glutamate Dysregulation and Glutamatergic Therapeutics for PTSD: Evidence from Human Studies. Neurosci Lett, 2017;649:147-155.
Reul JMHM, Nutt DJ. Glutamate and cortisol—a critical confluence in PTSD? Journal of Psychopharmacology, 2008;22(5):469-472.

\* cited by examiner

Pre and Post Treatment HAM-D scores for all subjects

GLUTAMATE AGENTS IN THE TREATMENT OF MENTAL DISORDERS

CROSS-REFERENCE TO RELATED APPLICATIONS

This application is a continuation application of U.S. patent application Ser. No. 14/278,573, filed 15 May 2014, which itself is a divisional application of U.S. patent application Ser. No. 11/399,188 filed on Apr. 5, 2006, which claims the benefit of U.S. Provisional Application No. 60/668,735, filed Apr. 5, 2005; U.S. Provisional Application No. 60/669,774, filed Apr. 7, 2005; U.S. Provisional Application No. 60/690,187, filed Jun. 13, 2005; U.S. Provisional Application No. 60/694,621, filed Jun. 27, 2005; and U.S. Provisional Application No. 60/756,472, filed Jan. 4, 2006; the teachings and specifications of which are incorporated herein by reference in their entireties.

BACKGROUND OF THE INVENTION

Anxiety disorders are often debilitating chronic conditions, which can be present from an early age or begin suddenly after a triggering event. They are prone to flare up at times of high stress. Anxiety disorders include panic disorder, agoraphobia, social anxiety disorder (also known as social phobia), specific phobia, or simple phobia, generalized anxiety disorder, obsessive-compulsive disorder, and post-traumatic stress disorder.

Many of these disorders can be treated with the aid of counseling and behavioral therapies, such as cognitive therapy. Such treatments may be used with or without adjunctive pharmaceutical therapy. A number of drugs have been used to treat these disorders, including benzodiazepines and antidepressants of all main classes: selective serotonin reuptake inhibitors ("SSRIs"), tricyclic antidepressants ("TCAs"), and monoamine oxidase inhibitors ("MAOIs").

Obsessive Compulsive Disorder ("OCD") is an example of an anxiety disorder. It is a debilitating psychiatric condition with a lifetime prevalence of 2-3%. It is characterized by recurrent, intrusive thoughts (obsessions) and/or repetitive, stereotyped behaviors (compulsions) that last for at least one hour per day and significantly interfere with an individual's normal level of functioning. Although cognitive behavioral therapy and pharmacotherapy with serotonin reuptake inhibitors (SRI) are effective treatments for many patients, a subset experience minimal relief from their symptoms with these standard treatments. When severe, OCD is completely incapacitating with devastating consequences for patients and their families. Augmentation strategies with neuroleptic medications can improve the effectiveness of SRI therapy but do not eliminate OCD symptoms (Saxena et al., *J. Clin. Psychiatry*, 57:303-6, 1996; McDougle et al., *J. Clin. Psychiatry*, 56:526-8, 1995) and are associated with adverse effects when used chronically. Consequently, improved pharmacological treatments are needed. The clinical observation that few patients experience a complete response to SRI's or dopamine antagonists suggests that other neurochemical systems are involved in the pathophysiology of OCD.

Thus, there is a need for pharmaceutical therapies that can be used to treat patients with the above disorders, including patients who do not respond to currently available therapies, as well as for pharmaceutical therapies that improve the efficacy of currently available treatment regimens.

SUMMARY OF THE INVENTION

The present invention solves these and other problems by providing methods of treating a mental disorder in an individual. In some aspects, the methods comprise administering to the individual an effective amount of a glutamate modulator. In certain embodiments, the disorder is an anxiety disorder, including obsessive-compulsive disorder. In some embodiments, the individual displays a particular score on the Yale Brown Obsessive Compulsive Scale or displays specific symptoms. In certain embodiments, the glutamate modulator attenuates presynaptic glutamate release or normalizes, enhances, or potentiates the uptake of glutamate by glia. In certain embodiments, the glutamate modulator is riluzole, N-acetylcysteine, a β-lactam, amantadine, lamictal, acamprosate, memantine, neramexane, remacemide, ifenprodil, or dextromethorphan. In certain specific embodiments, the β-lactam is a β-lactam antibiotic, such as penicillin, amoxicillin, ceftriaxone, cephapirin, cefoperazone, cefadroxil, bacampicillin, ampicillin, cephalothin, or nafcillin.

In another aspect, the invention provides methods of treating a mental disorder in an individual in need thereof. The methods comprise administering to the individual an effective amount of an agent that normalizes, enhances, or potentiates glutamate uptake by glia. In certain embodiments, the disorder is a specific mental disorder. In certain embodiments, the agent increases the expression, activity, or function of at least one glutamate transporter in glia. In specific embodiments, the agent is a glutamate modulating agent, including a β-lactam. In certain embodiments, the agent protects glial cells against glutamate toxicity, repletes levels of glutathione, or attenuates toxic levels of glutamate. In specific embodiments, the agent is N-acetylcysteine.

In yet another aspect, the invention provides methods of enhancing the activity of a serotonin reuptake inhibitor (SRI) in an individual in need thereof. The methods comprise co-administering to the individual a glutamate modulator and a SRI, wherein the glutamate modulator is administered in an amount sufficient to normalize synaptic glutamate levels in the individual, thereby resulting in greater activity of the SRI in the individual than would occur in the absence of co-administration of the glutamate modulator. In certain embodiments, the individual has an anxiety disorder, including obsessive-compulsive disorder. In certain embodiments, the glutamate modulator is riluzole, N-acetylcysteine, a β-lactam, amantadine, lamictal, acamprosate, memantine, neramexane, remacemide, ifenprodil, or dextromethorphan. In certain embodiments, the glutamate modulator is not riluzole. In certain embodiments, the serotonin reuptake inhibitor is citalopram, escitalopram, flouxetine, fluvoxamine, paroxetine, sertraline, trazodone, venlafaxine, mirtazepine, clomipramine, or combinations with other psychotropic medications including an anti-psychotic, an anti-convulsant, a tricyclic antidepressant, a monoamine oxidase inhibitor, a selective serotonin reuptake inhibitor, a selective serotonin-norepinephrine reuptake inhibitor, a norepinephrine dopamine reuptake inhibitor, a serotonin-2 antagonist reuptake inhibitor, a benzodiazepine, a wakefulness promoting agent, anti-manic agent, or a combination of one or more of the foregoing.

The invention also encompasses pharmaceutical compositions comprising a serotonin reuptake inhibitor and a glutamate modulator. In some embodiments, the serotonin reuptake inhibitor is citalopram, escitalopram, flouxetine, fluvoxamine, paroxetine, sertraline, trazodone, venlafaxine, mirtazepine, clomipramine, or combinations with other psychotropic medications including an anti-psychotic, an anticonvulsant, a tricyclic antidepressant, a monoamine oxidase inhibitor, a selective serotonin reuptake inhibitor, a selective serotonin-norepinephrine reuptake inhibitor, a norepinephrine dopamine reuptake inhibitor, a serotonin-2 antagonist reuptake inhibitor, a benzodiazepine, a wakefulness promoting agent, anti-manic agent, or a combination of one or more of the foregoing. In some embodiments, the glutamate modulator is riluzole, N-acetylcysteine, a β-lactam, amantadine, lamictal, acamprosate, memantine, neramexane, remacemide, ifenprodil, or dextromethorphan. In some embodiments, the pharmaceutical composition additionally comprises a pharmaceutically acceptable carrier.

The details of various aspects of the invention are set forth in the accompanying drawings and the description below. Other features, objects, and advantages of the invention will be apparent from the description and claims.

DETAILED DESCRIPTION

Mental Disorders

Figure 1:
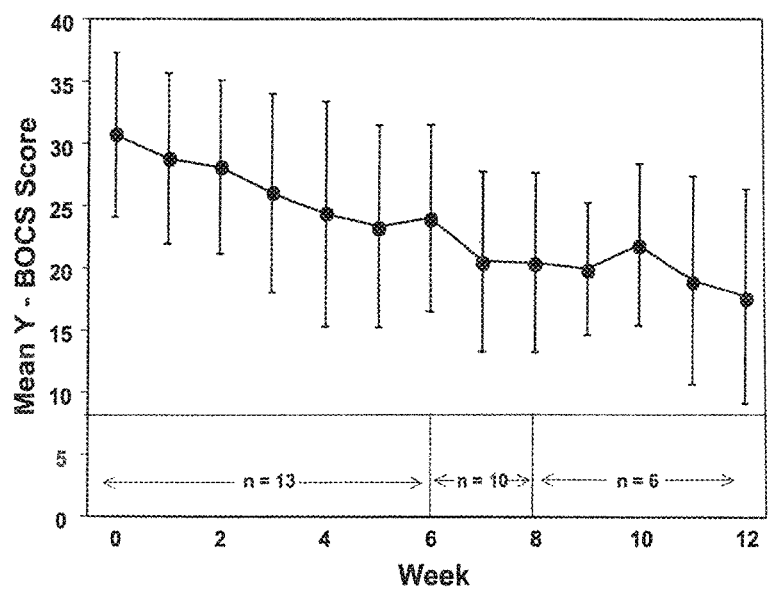
FIG. 1 shows the mean Y-BOCS score in patients with serotonin reuptake inhibitor-resistant obsessive-compulsive disorder treated with riluzole addition.

The methods and compositions of the instant invention are useful in the treatment of various mental disorders. Such disorders are defined and categorized in the *Diagnostic and Statistical Manual of Mental Disorders*, 4$^{th}$ Ed., Text Revision ("DSM-IV-TR"), American Psychiatric Association, Washington, D.C., 2000. The term "mental disorder", as used herein, is not intended to imply a distinction between "physical" and "mental" disorders and is considered to encompass the full breadth of disorders described in DSM-IV-TR. Examples of classes of mental disorders usefully treated by to the methods and compositions of the instant invention include, e.g., disorders usually first diagnosed in infancy, childhood, or adolescence; delirium, dementia, or amnestic or other cognitive disorders; mental disorders due to a general medical condition; substance-related disorders; schizophrenia or other psychotic disorders; mood disorders; anxiety disorders; somatoform disorders; factitious disorders; dissociative disorders; sexual or gender identity disorders; eating disorders; sleep disorders; impulse-control disorders; and adjustment disorders. In certain embodiments, the methods and compositions of the invention are used to treat mood disorders and anxiety disorders. In some embodiments, the mood disorder is major depression disorder. In some embodiments, the anxiety disorder is obsessive-compulsive disorder. Other disorders that can be treated using the methods and compositions of the instant invention include bipolar disorder, schizophrenia, tic disorders, Tourette's disorder, generalized anxiety disorder, and other neuropsychiatric disorders. In some embodiments of the invention, the individual does not have major depressive disorder. In some embodiments, the individual has more than one disorder.

In some embodiments of the invention, the individual treated according to the claimed method is assessed using the Yale Brown Obsessive Compulsive Scale ("Y-BOCS"). See Goodman et al., *Arch. Gen. Psychiatry* 46:1006-1011, 1989. According to this system, an individual is scored using a symptom checklist by asking the individual about specific obsessions and compulsions. Such symptoms are broadly categorized as aggressive obsessions, contamination obsessions, sexual obsessions, hoarding/saving obsessions, religious obsessions, obsession with need for symmetry or exactness, miscellaneous obsessions, somatic obsessions, cleaning/washing compulsions, checking compulsions, repeating rituals, counting compulsions, ordering/arranging compulsions, and miscellaneous compulsions. Each of these categories is further divided by subcategory of more specific symptoms. Individuals are scored according to the answers provided. Scores range from 0-7 for subclinical, 8-15 for mild, 16-23 for moderate, 24-31 for severe, and 32-40 for extreme severity. In some embodiments of the invention, the individual displays a Yale Brown Obsessive Compulsive Scale score of at least 20 prior to treatment. In other embodiments, the individual displays a score of at least 24, at least 28, at least 32, or at least 36 prior to treatment.

According to the Y-BOCS system, the broad symptom categories may be further subdivided. Subcategories of aggressive obsessions include: fear might harm self; fear might harm others; violent or horrific images; fear of blurting out obscenities or insults; fear of doing something else embarrassing; fear will act on unwanted impulses (e.g., to stab friend); fear will steal things; fear will harm others because not careful enough; (e.g. hit/run motor vehicle accident); and fear will be responsible for something else terrible happening (e.g., fire, burglary). Subcategories of contamination obsessions include: concerns or disgust w\ with bodily waste or secretions (e.g., urine, feces, saliva), concern with dirt or germs; excessive concern with environmental contaminants (e.g. asbestos, radiation toxic waste); excessive concern with household items (e.g., cleansers solvents); excessive concern with animals (e.g., insects); bothered by sticky substances or residues; concerned will get ill because of contaminant; concerned will get others ill by spreading contaminant (aggressive); and no concern with consequences of contamination other than how it might feel. Subcategories of sexual obsessions include: forbidden or perverse sexual thoughts, images, or impulses; content involves children or incest; content involves homosexuality; and sexual behavior towards others (aggressive). Subcategories of religious obsessions include: concerned with sacrilege and blasphemy; and excess concern with right/wrong, morality. Subcategories of obsession with need for symmetry of exactness include: accompanied by magical thinking (e.g., concerned that another will have accident dent unless things are in the right place); and not accompanied by magical thinking. Subcategories of miscellaneous obsessions include: need to know or remember; fear of saying certain things; fear of not saying just the right thing; fear of losing things; intrusive (nonviolent) images; intrusive nonsense sounds, words, or music; bothered by certain sounds/noises; lucky/unlucky numbers; colors with special significance; and 3 superstitious fears.

Subcategories of somatic obsessions include: concern with illness or disease; and excessive concern with body part or aspect of appearance (eg., dysmorphophobia). Subcategories of cleaning/washing compulsions include: excessive or ritualized handwashing; excessive or ritualized showering, bathing, toothbrushing grooming, or toilet routine, involves cleaning of household items or other inanimate objects; and other measures to prevent or remove contact with contaminants. Subcategories of checking compulsions include: checking locks, stove, appliances etc.; checking that did rot/will not harm others; checking that did not/will not harm self; checking that nothing terrible did/will happen; checking that did not make mistake; and checking tied to somatic obsessions. Subcategories of repeating rituals include: rereading or rewriting; and need to repeat routine activities (jog, in/out door, up/down from chair). Subcategories of miscellaneous compulsions include: mental rituals (other than checking/counting); excessive listmaking; need to tell, ask, or confess; need to touch, tap, or rub; rituals involving blinking or staring; measures (not checking) to prevent: harm to self—harm to others terrible consequences; ritualized eating behaviors; superstitious behaviors; Trichotillomania; other self-damaging or self-mutilating behaviors.

Glutamate Modulators

The glutamate modulators of the instant invention are agents that normalize glutamate levels in an individual to whom they are administered. Glutamate modulators of utility in the invention include, for example, agents that attenuate or normalize presynaptic glutamate release or that normalize, enhance, or potentiate the uptake of glutamate by glia. The term is also intended to encompass any agent that attenuates or normalizes the intracellular modulators of the response to glutamate (e.g., protein kinase C ("PKC") inhibitors, calcium channel blockers, inhibitors of voltage gated sodium channels, inhibitors of voltage gated calcium channels, and N P Q voltage gated calcium channels). The term is also intended to encompass agents that are antagonists at AMPA receptors, agents that modulate IP3 or ryanodine receptors, agents that act as mGlu Group I receptor antagonists, agents that act as mGlu receptor Group II and III agonists, and agents that act on the cysteine-glutamate antiporter.

In some embodiments, the glutamate modulator is an agent that increases excitatory amino acid transporter function. In specific embodiments, the glutamate modulator is an agent that enhances function or expression of excitatory amino acid transporters (EAAT) located on glia and neurons.

In some embodiments of the invention, the glutamate modulator is riluzole, N-acetylcysteine, a β-lactam, amantadine, lamictal, acamprosate, memantine, neramexane, remacemide, ifenprodil, or dextromethorphan.

In more specific embodiments of the invention, the glutamate modulator is riluzole.

In other embodiments, the glutamate modulator is N-acetylcysteine, β-lactam, amantadine, lamictal, acamprosate, memantine, neramexane, remacemide, ifenprodil, or dextromethorphan. The β-lactam may be a β-lactam antibiotic, such as, for example, penicillin, amoxicillin, ceftriaxone, cephapirin, cefoperazole, cefadroxil, bacampicillin, ampicillin, cephalothin, or nafcillin. In specific embodiments, the glutamate modulator is ceftriaxone.

The β-lactams of the invention include those β-lactam compounds that are known in the art. See, e.g., U.S. Pat. Nos. 5,310,897 and 6,031,094. These and other β-lactams of the invention may be synthesized by standard chemical techniques as is well known in the art. In some cases, the β-lactams are β-lactam antibiotics.

In some embodiments of the invention, the glutamate modulator includes more than one of the above-defined glutamate modulators.

The glutamate modulators of the instant invention may contain one or more asymmetric elements such as stereogenic centers or stereogenic axes e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms; all isomeric forms of the compounds are included in the present invention. In these situations, the single enantiomers (optically active forms) can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

Unless otherwise specified, or clearly indicated by the text, a glutamate modulator of the instant invention includes the free base or free acid forms of the modulator, if any, as well as any and all pharmaceutically acceptable salt forms of the modulator. Such salt forms include derivatives of the modulator, wherein the parent compound is modified by making non-toxic acid or base addition salts thereof, and also include pharmaceutically acceptable solvates, including hydrates, of such compounds and such salts. Examples of pharmaceutically acceptable salt forms include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, and nitric; other acceptable inorganic salts include metal salts such as sodium salt, potassium salt, and cesium salt; and alkaline earth metal salts, such as calcium salt and magnesium salt; and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4; organic amine salts such as triethylamine salt, pyridine salt, picoline salt, ethanolamine salt, triethanolamine salt, dicyclohexylamine salt, N,N'-dibenzylethylenediamine salt; and amino acid salts such as arginate, asparginate, and glutamate, and combinations comprising one or more of the foregoing salts.

The compounds of the invention may be synthesized using conventional techniques. Advantageously, these compounds are conveniently synthesized from readily available starting materials.

As used herein, the compounds of the invention are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention, which, upon administration to a recipient, is capable of providing or provides (directly or indirectly) a compound of this invention.

Accordingly, this invention also provides prodrugs of the compounds of the invention, which are derivatives that are designed to enhance biological properties such as oral absorption, clearance, metabolism or compartmental distribution. Such derivations are well known in the art.

As the skilled practitioner realizes, the compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The term "protected" refers to the attachment of a suitable chemical group (protecting group) to the designated functional group. Examples of suitable amino protecting groups and protecting groups are described in Greene and Wuts, *Protective Groups in Organic Synthesis*, 2d. Ed., John Wiley and Sons, 1991; Fieser and Fieser, *Fieser and Fieser's Reagents for Organic Synthesis*, John Wiley and Sons, 1994; Paquette, ed. *Encyclopedia of Reagents for Organic Synthesis*, John Wiley and Sons, 1995.

Certain derivatives and prodrugs are those that increase the bioavailability of the compounds of the invention when such compounds are administered to an individual (e.g., by allowing an orally administered compound to be more readily absorbed into the blood), have more favorable clearance rates or metabolic profiles, or enhance delivery of the parent compound to a biological compartment (e.g., the brain or lymphatic system) relative to the parent species. Examples of prodrugs include derivatives in which a group that enhances aqueous solubility or active transport through the gut membrane is appended to the structure.

Serotonin Reuptake Inhibitors

The methods and compositions of the invention relate to the use of glutamate modulators to enhance the activity of a serotonin reuptake inhibitor ("SRI"). SRIs, including selective SRIs ("SSRIs") are well known in the art and are widely used in the treatment of mood disorders, as well as in the treatment of other mental disorders. In one aspect of the invention, the activity of an SRI is enhanced in an individual in need thereof. The method comprises co-administering to the individual a glutamate modulator and a SRI, wherein the glutamate modulator is administered in an amount sufficient to normalize synaptic glutamate levels in the individual, thereby resulting in greater activity of the SRI in the individual than would occur in the absence of co-administration of the glutamate modulator. In a specific embodiment of the invention, the SRI is citalopram, escitalopram, flouxetine, fluvoxamine, paroxetine, sertraline, trazodone, venlafaxine, mirtazepine, clomipramine, or combinations with other psychotropic medications including an anti-psychotic, an anti-convulsant, a tricyclic antidepressant, a monoamine oxidase inhibitor, a selective serotonin reuptake inhibitor, a selective serotonin-norepinephrine reuptake inhibitor, a norepinephrine dopamine reuptake inhibitor, a serotonin-2 antagonist reuptake inhibitor, a benzodiazepine, a wakefulness promoting agent, anti-manic agent, or a combination of one or more of the foregoing.

Administration and Dosage

The methods and compositions of the instant invention are used to treat individuals of any mammalian species, including domestic livestock, such as horses, cattle, sheep, pigs, goats, bison, model experimental animals, such as mice, rats, guinea pigs, and rabbits, domestic pets such as dogs and cats, and human beings. The methods and compositions are preferably used to treat human beings.

The term "treating" as used herein refers to the lessening or alleviation of symptoms of a particular disorder in an individual or the improvement of an ascertainable measurement associated with a particular disorder.

In one aspect, the invention provides pharmaceutical compositions comprising a serotonin reuptake inhibitor and a glutamate modulator. An alternate embodiment provides compositions comprising a serotonin reuptake inhibitor, a glutamate modulator, and a pharmaceutically acceptable carrier.

The term "pharmaceutically acceptable carrier" refers to a carrier that may be administered to a patient, together with a compound of this invention, and which does not destroy the pharmacological activity of the compound and is non-toxic when administered in doses sufficient to deliver a therapeutic amount of the compound.

Pharmaceutically acceptable carriers that may be used in the pharmaceutical compositions of this invention include, but are not limited to, ion exchangers, alumina, aluminum stearate, lecithin, self-emulsifying drug delivery systems (SEDDS) such as α-tocopherol, polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of the compounds of the invention.

The pharmaceutical compositions of this invention may be administered orally, parenterally, by inhalation spray, topically, rectally, nasally, buccally, vaginally or via an implanted reservoir. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica (Ph. Helv.) or a similar alcohol, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of the present invention may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient that can be combined with a carrier material to produce a single dosage form will generally be that amount of the compound that produces a therapeutic effect. Generally, out of one hundred percent, this amount will range in some embodiments from about 1 percent to about ninety-nine percent of active ingredient, in some embodiments from about 5 percent to about 70 percent, and in some embodiments from about 10 percent to about 30 percent.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, gender, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In some embodiments, the active compound will be administered once daily.

In another aspect of the invention, the compounds of the invention are administered alone or co-administered with another therapeutic agent. As used herein, the phrase "co-administration" refers to any form of administration of two or more different therapeutic compounds such that the desired effect is obtained. For example, the second compound is administered while the previously administered therapeutic compound is still effective in the body (e.g., the two compounds are simultaneously effective in the patient, which may include synergistic effects of the two compounds). The different therapeutic compounds may be administered either in the same formulation or in a separate formulation, either concomitantly or sequentially. Thus, an individual who receives such treatment may benefit from a combined effect of different therapeutic compounds. Co-administration includes simultaneous or sequential administration of two or more compounds.

In certain embodiments, a glutamate modulator of the present invention is co-administered with a serotonin reuptake inhibitor. The serotonin reuptake inhibitor is, for example, citalopram, escitalopram, flouxetine, fluvoxamine, paroxetine, sertraline, trazodone, venlafaxine, mirtazepine, clomipramine, or combinations with other psychotropic medications including an anti-psychotic, an anti-convulsant, a tricyclic antidepressant, a monoamine oxidase inhibitor, a selective serotonin reuptake inhibitor, a selective serotonin-norepinephrine reuptake inhibitor, a norepinephrine dopamine reuptake inhibitor, a serotonin-2 antagonist reuptake inhibitor, a benzodiazepine, a wakefulness promoting agent, anti-manic agent, or a combination of one or more of the foregoing.

Effects of Glutamate Modulators

The glutamate modulators of the instant invention may usefully attenuate presynaptic glutamate release or normalize, enhance, or potentiate the uptake of glutamate by glia. Without intending to be bound by theory, it is believed that agents that reduce glutamate hyperactivity, or its consequences, in the central nervous system might be efficacious as therapeutic interventions. See, e.g., Pittenger et al., *The Journal of the American Society for Experimental NeuroTherapeutics* 3:69-81, 2006. Such agents are especially useful in the treatment of individuals with obsessive-compulsive disorder and, in particular, those individuals that are resistant to treatment with other agents, such as serotonin reuptake inhibitors. Coric et al., *Psychopharmacology.* 167: 210-220, 2003. Coric et al., *Biological Psychiatry.* 58:424-428, 2005.

In some embodiments of the invention, the glutamate modulators of the invention attenuate presynaptic glutamate release. For example, riluzole is FDA-approved as a neuroprotectant in the treatment of amyotrophic lateral sclerosis ("ALS"). The pharmacology of riluzole includes: 1) an inhibitory effect on glutamate release, 2) inactivation of voltage-dependent sodium channels, and 3) ability to interfere with intracellular events that follow transmitter binding at excitatory amino acid receptors. See *Physician's Desk Reference,* 59$^{th}$ Ed, 744-746, 2005, Thomson, Montvale, N.J. In some embodiments of the invention, the glutamate modulators of the invention normalize, enhance, or potentiate the uptake of glutamate by glia. For example, N-acetylcysteine is widely used for its antioxidant properties and as an antidote for acetaminophen toxicity. See U.S. Pat. No. 6,566,401. It also modulates CNS glutamate (Pittenger et al., *The Journal of the American Society for Experimental NeuroTherapeutics* 3:69-81, 2006) and is effective in treating SRI-refractory obsessive-compulsive disorder (see below). Without intending to be bound by theory, N-acetylcysteine may cause glial release of glutamate into the extrasynaptic space, where it may stimulate inhibitory metabotropic glutamate receptors on glutamatergic nerve terminals and thus reduce the synaptic release of glutamate. Pittenger et al., *The Journal of the American Society for Experimental Neuro Therapeutics* 3:69-81, 2006. N-acetylcysteine may also protect glial cells against glutamate toxicity, replete levels of glutathione, and attenuate toxic levels of glutamate. Id. In some embodiments of the invention, the glutamate modulators of the invention increase the expression, activity, or function of at least one glutamate transporter in glia. For example, β-lactam antibiotics upregulate the glial glutamate uptake transporter and display neuroprotective effects in a mouse model of ALS. Rothstein et al., *Nature,* 433:73-77, 2005.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Example, which is included herewith for purposes of illustration only and is not intended to be limiting of the invention.

Example 1

Riluzole Augmentation in Treatment-Resistant Obsessive-Compulsive Disorder

Methods and Materials

Thirteen patients were recruited from the Yale OCD Research Clinic. Patient characteristics and inpatient/outpatient status are listed in Table 1. All patients provided written informed consent prior to study participation. The study was approved by the Yale University Human Investigations Committee, New Haven, Conn. Patients between the ages 18 and 65 with a primary DSM-IV diagnosis of OCD who had failed to clinically respond to at least eight weeks of treatment with SRIs were eligible for study participation. Treatment failure was defined by a Yale-Brown Obsessive Compulsive Scale (Y-BOCS) score >16 despite at least eight weeks of treatment with the maximum tolerated dose of an SRI medication. Additionally, OCD symptoms had to be present for at least one year and at least of moderate severity on the Clinical Global Impression Scale severity of illness item. Patients with a primary psychotic disorder, prior psychosurgery for OCD, illicit substance use over the past one month, seizure disorder, significant head trauma, acute medical illnesses, or elevated baseline LFT's (i.e., greater than twice the upper limits of normal) were excluded from study participation. Diagnoses were confirmed using the Structured Clinical Interview for Axis I DSM-IV Disorders. Major depression was the most common comorbid diagnosis, occurring in 10 of the 13 patients. Patients had to have failed at least eight weeks of treatment on their current SRI medication. Concomitant psychotropic medications were permitted only if prescribed at a stable dose for at least one month prior to beginning the trial.

Study duration was initially six weeks. After results from initial subjects suggested ongoing therapeutic response with time, the study was extended to nine weeks and then to twelve weeks.

Riluzole was initiated and maintained at a dose of 50 mg twice a day. Subjects were evaluated weekly with clinician-administered rating scales: Y-BOCS, Clinical Global Impression/Global Improvement item (CGI/GI), Hamilton Depression Inventory (HAM-D), and Hamilton Anxiety Inventory (HAM-A). Liver function tests were monitored at baseline and every three weeks throughout the study. Because of the variable time of treatment (6-12 weeks), Y-BOCS, HAM-D and HAM-A were analyzed in SAS PROC MIXED using mixed effects models with time (baseline to week 9) as fixed effect and a structured variance-covariance pattern matrix (Gueorguieva and Krystal, *Archives of General Psychiatry* 61: 310-317, 2004; Brown and Prescott, *Applied Mixed Models in Medicine*, John Wiley & Sons 1999; New York, N.Y.). CGI/GI was analyzed using the same model with time (baseline to week 7) as fixed effect. The best fitting variance-covariance matrix according to the Akaike Information Criterion was selected.

Results

Thirteen patients entered the study and only one subject, a treatment responder, dropped out at week nine due to a family situation. Previous SRI treatment trials, history of augmentation strategies, previous cognitive behavioral therapy, dosage of concomitant medications, and outcome variables for each patient are shown in Table 2. The mean number of previously failed medication trials included 3.5 (±1.7) SRI/SNRI/TCA trials and 1.3 (±1.5) dopamine antagonist augmentation trials. Additionally, twelve of thirteen subjects failed previous trials of cognitive behavioral therapy. Mean doses of concomitant medications during the study, dosed alone or in combination, included: fluoxetine 80 mg (n=4), clomipramine 262.5 mg (n=4), escitalopram 20 mg (n=2), fluvoxamine 300 mg (n=3), buspirone 30 mg (n=1), risperidone 5 mg (n=1), olanzapine 11.3 mg (n=2), quetiapine 50 mg (n=1), and clonazepam 1.3 mg (n=5). Mean Y-BOCS score of patients entering the study was 30.7 (±6.6), indicating severe OCD symptoms. Data from one patient was previously published as a case report (Coric et al. 2003).

FIG. 1 illustrates the mean Y-BOCS score for all study participants. Mean Y-BOCS for the group at baseline was 30.7 (±6.6) and at end of study was 17.7 (±8.6), representing an overall 42% reduction for the entire cohort. Y-BOCS scores improved significantly over time ($F_{1,11.1}=19.78$, $p=0.001$). Seven of thirteen patients (54%) demonstrated a >35% reduction in Y-BOCS scores. Five of thirteen patients (39%) were categorized as treatment responders, as defined by a 35% or greater reduction in baseline Y-BOCS, a final Y-BOCS of 16 or less, and consensus of the treating clinicians. Percent reduction in baseline Y-BOCS scores at end of study ranged from 38-76% in responders. Two out of the five responders were characterized predominantly by hoarding behaviors. Clinician administered CGI/GI scores significantly improved over time ($F_{1,16.2}=20.99$, $p=0.0003$). Mean baseline CGI/GI was 4 (±0), week 6 CGI/GI was 3.2 (±0.6), week 9 CGI/GI was 2.66 (±0.5), and week 12 CGI/GI was 2.33 (±1).

Figure 2:
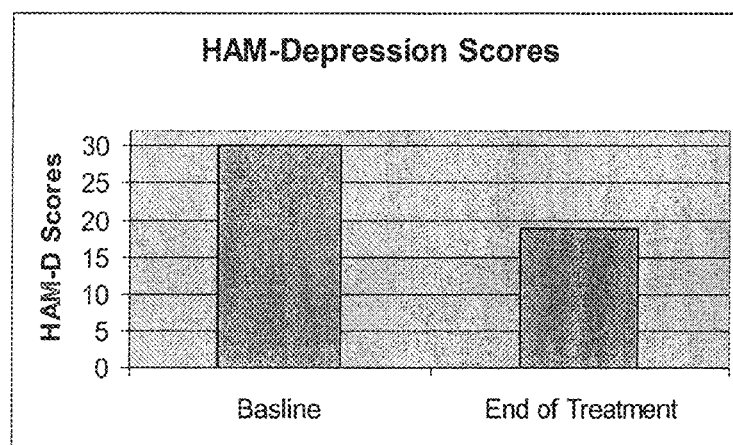
FIG. 2 shows pre- and post-treatment HAM-D scores in patients with serotonin reuptake inhibitor-resistant obsessive-compulsive disorder treated with riluzole addition.

Mean HAM-D at baseline was 30 (±13.7) and at end of study was 19.7 (±6.0). FIG. 2. HAM-D scores for the entire group improved significantly over time ($F_{1,10.8}=9.12$, $p=0.012$); six out of thirteen patients demonstrated clinically significant improvements in HAM-D scores with 36-83% reductions in baseline HAM-D scores by the end of the study. Mean HAM-A at baseline was 18.2 (±6.2) and at end of study was 12 (±2.5). HAM-A scores improved significantly over time ($F_{1,11.2}=7.9$, $p=0.017$). Riluzole was well tolerated and no serious adverse events were noted. Asymptomatic, transient increases in at least one LFT were noted in four of thirteen patients. One patient experienced a nine-fold increase in ALT; repeat ALT in that patient revealed a four-fold increase that normalized to within nine times the upper limits of normal by week three. Mean baseline AST, ALT, and Alk Phos were 19.1 (±5.7), 22.9 (±12.3), 75 (±13.5), respectively; Mean week six AST, ALT, and Alk Phos were 22 (±13.84), 35.3 (±28.3), 83.7 (±24.4).

Figure 3:
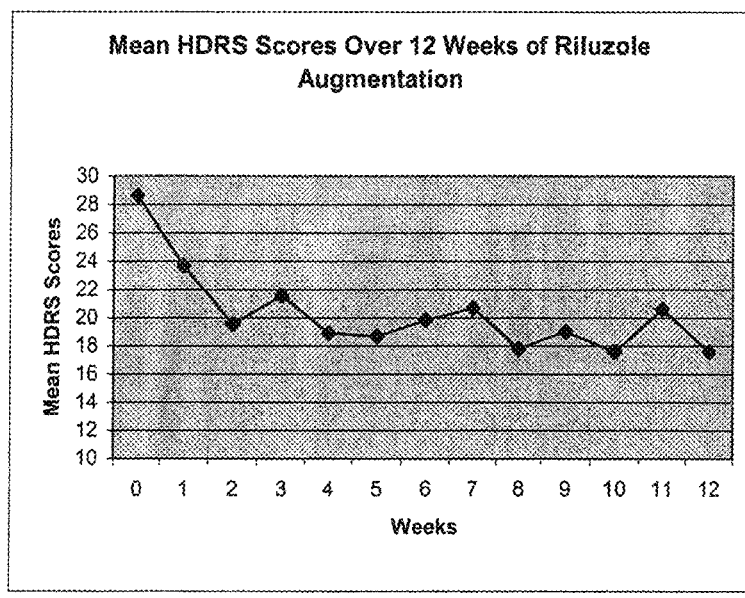
FIG. 3 shows HAM-D scores in treatment-resistant depression patients treated with riluzole addition.
Figure 4:
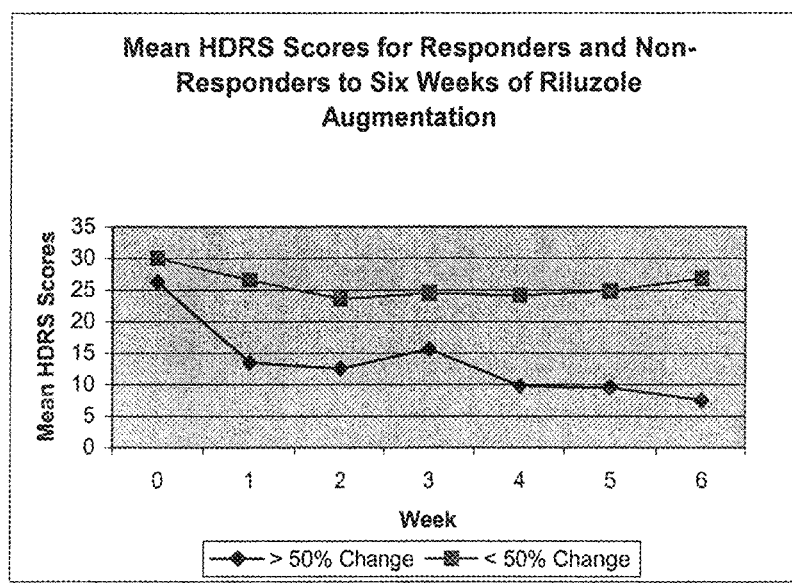
FIG. 4 shows compares HAM-D scores for responders (diamond symbols) and non-responders (square symbols) in treatment-resistant depression patients treated with riluzole addition.

A control group of patients with treatment-resistant depression alone also showed significant improvement of HAM-D scores in response to riluzole in this study. See FIGS. 3 and 4.

TABLE 1

Clinical Characteristics of Patients with OCD Treated with Riluzole Addition to SRI

| Patient No./Age(y)/Sex/Ethnicity | Age at onset of OCD (y) | Duration of OCD (y) | Type of OCD Symptoms | Comorbid Diagnoses | Psychiatric Family History |
|---|---|---|---|---|---|
| 001/34/M/W‡ | 11 | 23 | Agg, sex | MDD | OCD (p grandfather); anorexia (sister) |
| 002/53/F/W‡ | 48 | 5 | Agg, sex | MDD, Tic | Suicide (p grandfather, p uncle) |
| 003/29/M/W | 10 | 19 | Agg, ctm, rel, cln/was, chk, cnt, ntk | MDD, Tic | OCD (father) |
| 004/50/F/W | 23 | 27 | Sym/ext, ord/arr | MDD | None |
| 005/36/M/W‡ | 22 | 14 | Chk, rpt, ntk | None | OCD (father); MDD (mother); Panic Disorder (father); GAD (brother, sister) |
| 006/23/F/W‡ | 22 | 1 | Som, ctm, cln/was | MDD | None |
| 007/61/F/W | 30 | 31 | Hrd, sym/ext, chk, rpt, cnt, ord/arr, ntk | None | OCD (mother); alcohol abuse (father) |

TABLE 1-continued

Clinical Characteristics of Patients with OCD Treated with Riluzole Addition to SRI

| Patient No./ Age(y)/Sex/ Ethnicity | Age at onset of OCD (y) | Duration of OCD (y) | Type of OCD Symptoms | Comorbid Diagnoses | Psychiatric Family History |
|---|---|---|---|---|---|
| 008/30/M/W‡ | 16 | 14 | Agg, sex, rel, chk, cnt | MDD | None |
| 009/61/F/AA | 43 | 18 | Hrd, rel | MDD | None |
| 010/29/F/W‡ | 18 | 11 | Cln/was, cnt, sym/ext, chk, cnt, rpt, hrd | MDD | OCD (m grandfather); schizophrenia (p grandmother) |
| 011/46/F/W‡ | 24 | 22 | Ctm, hrd, cln/was, chk, sym/ext | None | None |
| 012/30/F/W | 22 | 8 | Chk, sym/ext, rpt, ord/arr, ntr | MDD | None |
| 013/50/M/W‡ | 21 | 29 | Sym/ext, ctm, cln/was, hrd, chk, rpt, ord/arr, ntk | MDD | MDD (father, m grandmother + father, p aunt + uncle); alcohol abuse (father) |

OCD, obsessive-compulsive disorder; MDD, major depressive disorder; GAD, generalized anxiety disorder; Panic, Panic Disorder; Tic, Tic Disorder; M, male; F, female; W, Caucasian; AA, African-American; m, maternal; p, paternal
Agg indicates aggressive; sym/ext, symmetry/exactness; chk, checking; ntk, need to know; rpt, repeating; ord/arr, ordering/arranging; ctm, contamination; cln/wsh, cleaning/washing; som, somatic; rel, religious; hrd, hoarding; cnt, counting; ntr, need to touch, tap, or rub; and sex, sexual.
‡Treated as inpatient

TABLE 2

Treatment Data of Patients with OCD treated with Riluzole Addition to SRI

| Pt No. | No. of Previous Medication Trials | Previous SRI Treatment Trials | Previous Neuroleptic Augmentat. | Previous Behavioral Therapy | Current SRI | Daily SRI Dose | Concommittant Medications | CGI Treatment Response | Pre/Post YBOCS Score | Pre/Post HAM-D Score | Pre/Post HAM-A Score |
|---|---|---|---|---|---|---|---|---|---|---|---|
| 1[b] | 4 | Citalopram, fluvoxamine, venlafaxine | Yes | Yes | Fluvoxamine | 300 mg | Clonazepam 1 mg qhs | 3 | 19/11* | 52/33* | 22/20 |
| 2[b] | 3 | Sertraline | Yes | No | Clomipramine | 350 mg | Olanzapine 7.5 mg qhs | 4 | 18/14* | 37/25 | 18/15 |
| 3[b] | 6 | Fluvoxamine, fluoxetine, paroxetine, citalopram, sertraline, venlafaxine | Yes | Yes | Clomipramine | 225 mg | Buspar 30 mg qhs | 3 | 35/34 | 12/12 | 7/3* |
| 4[a] | 7 | Sertraline, fluoxetine, citalopram, paroxetine, escitalopram, clomipramine, fluvoxamine | Yes | Yes | Escitalopram | 20 mg | None | 4 | 40/39 | 25/29 | 14/31 |
| 5[b] | 4 | Fluvoxamine, clomipramine, buspirone | No | Yes | Fluoxetine | 80 mg | Quetiapine 50 mg qhs | 3 | 32/28 | 15/13 | 14/14 |
| 6[a] | 2 | Escitalopram | Yes | Yes | Escitalopram | 20 mg | Risperidone 5 mg qhs | 2 | 37/16* | 56/16* | 25/8* |
| 7[c] | 2 | Fluoxetine | No | Yes | Fluoxetine | 80 mg | None | 3 | 31/13* | 17/20 | 13/12 |
| 8[c] | 5 | Sertraline, fluvoxamine, paroxetine, clomipramine | Yes | Yes | Clomipramine | 250 mg | Olanzapine 15 mg qhs, Clonazepam 0.5 mg tid | 3 | 35/32 | 28/30 | 22/15 |
| 9[c] | 3 | Fluvoxamine, fluoxetine | No | Yes | Fluoxetine | 80 mg | None | 1 | 33/8* | 41/11* | 29/10* |
| 10[c] | 2 | Fluvoxamine | Yes | Yes | Fluvoxamine | 300 mg | Clonazepam 0.5 mg bid | 3 | 32/20* | 31/20* | 19/15 |
| 11[c−] | 1 | Fluoxetine | No | Yes | Fluoxetine | 80 mg | Clonazepam 0.5 mg qid | 2 | 34/20* | 18/3* | 11/4* |
| 12[c] | 4 | Fluoxetine, escitalopram, fluvoxamine, paroxetine | Yes | Yes | Clomipramine | 225 mg | Topiramate 50 mg bid, Clonazepam 1 mg qhs | 2 | 28/21 | 25/19 | 18/11* |

TABLE 2-continued

Treatment Data of Patients with OCD treated with Riluzole Addition to SRI

| Pt No. | No. of Previous Medication Trials | Previous SRI Treatment Trials | Previous Neuroleptic Augmentat. | Previous Behavioral Therapy | Current SRI | Daily SRI Dose | Concommittant Medications | CGI Treatment Response | Pre/Post YBOCS Score | Pre/Post HAM-D Score | Pre/Post HAM-A Score |
|---|---|---|---|---|---|---|---|---|---|---|---|
| 13[c] | 3 | Paroxetine, fluvoxamine, clomipramine | No | Yes | Fluvoxamine | 300 mg | None | 2 | 25/12* | 33/18* | 24/9* |

Abbreviations: YBOCS, Yale Brown Obsessive Compulsive Scale; Ham-D, Hamilton Depression Rating Scale; Ham-A, Hamilton Anxiety Rating Scale; CGI, Clinical Global Impressions; bid, two times a day; tid, three times a day; qid, four times a day; qhs, given at bedtime
*>35% reduction in pre/post rating scales
[a]Study duration 6 weeks
[b]Study duration 9 weeks
[c]Study duration 12 weeks
[c~]Subject enrolled for 12 week study, responded to treatment, and dropped from study at week 9 due to family situation (represents the only study drop-out)

Discussion

This open label study suggests that directly attenuating glutamatergic activity may be efficacious in treatment-resistant OCD. Furthermore, the observed improvements in Y-BOCS, HAM-D, and HAM-A scores after addition of riluzole is consistent with recent clinical reports suggesting that modulation of glutamatergic pathways using the antiglutamatergic agent riluzole may provide symptom relief in anxiety and mood disorders (Coric et al., *Psychopharmacology* 167:210-220, 2003; Sanacora et al., *Am J Psychiatry.* 161(11):2132, 2004; Zarate et al., *Am. J. Psych.* 161:171-4, 2004).

Effective OCD treatment with SRI medications has been observed to lead to a reduction in glutamatergic tone in the CST network (Rosenberg et al., *J. Am. Acad. Child Adolesc. Psychiatry* 39(9):1096-103, 2000). Although OCD has been associated with increased activity in the CST network, it may not be associated with a global increase in glutamatergic function. In fact, a recent report shows reduced glutamate concentrations in the anterior cingulate gyrus in both OCD and major depression (Rosenberg et al., *J. Am. Acad. Child Adolesc. Psychiatry* 43(9):1146-53, 2004). Further study is required to determine whether riluzole preferentially targets components of the CST circuitry or has a more global effect. Additionally, the role of glutamate in the pathophysiology of mood and anxiety disorders is yet to be elucidated. The relationship between glutamate or Glx levels measured with $^1$H-MRS and the rate of glutamatergic neurotransmission is also far from clear (Seibyl et al., *Neurobiology of Mental Illness*, Charney et al., eds., Oxford Univ. Press, NY, 170-189, 2001). Glutamate is present in all brain cells, where it participates in a number of cellular functions unrelated to neurotransmission. While glutamate is the substrate for glutamatergic neurotransmission, it is not clear whether increases or decreases in glutamate levels measured by $^1$H-MRS reflect increased synaptic glutamate release. The extent to which synaptic or extrasynaptic glutamate contribute to the $^1$H-MRS glutamate signal is unknown. We hypothesize that riluzole may reduce synaptic glutamate by attenuating elevations in extrasynaptic glutamate levels that may arise as a consequence of impairment of glial glutamate uptake (Sanacora et al., *Ann. N.Y. Acad. Sci.* 1003:292-308, 2003). Thus, the antidepressant efficacy of riluzole could be consistent with studies describing elevations (Sanacora et al., *Arch. Gen. Psychiatry,* 61:705-713, 2004) or decreases (Auer et al., *Biol. Psychiatry* 47(4):305-13, 2000) in cortical glutamate levels. Future studies employing $^{13}$C-MRS that can separate glial and neuronal metabolic rates will be needed to define the nature of glutamatergic disturbances in OCD and depression (Lebon et al., *J. Neurosci.* 22(5):1523-31, 2002; Shen et al., *Proc. Natl Acad. Sci. USA.* 96(14): 8235-40, 1999).

The most common comorbid psychiatric illness in the current study was major depressive disorder (MDD). Studies suggest that the presence of MDD in patients with OCD negatively affects treatment outcome (Foa et al., *J. Consult. Clin. Psychol.* 51:287-297, 1983; Overbeck et al., *J. Clin. Psychiatry* 63:1106-1112, 2002). With recent estimates of the comorbidity between OCD and MDD ranging from 21 to 54% (Abramowitz, *J. Clin. Psychol.* 60:1133-1141, 2004), the higher than expected percentage of study subjects with these comorbid disorders (77%) likely reflects the severity of treatment resistance in our study population. It is important to note that the efficacy of riluzole augmentation in treatment-resistant OCD remained significant even when covarying for the magnitude of antidepressant effect in the current study. The clinical observation that SRIs, dopamine antagonists and now riluzole are useful for both mood and OCD symptoms suggests a partial overlap between the pathophysiology of these disorders.

Riluzole was well tolerated in our study and no patients discontinued treatment due to adverse effects. Riluzole is generally associated with transient elevations in LFTs; more than 50% of patients treated with riluzole experience elevations in at least one LFT measure and approximately 2% experience LFT elevations greater than five times the upper limit of normal (Aventis 2004). According to the *Physician's Desk Reference*, LFTs should be monitored every month during the first three months of treatment, every three months during the remainder the first year, and then periodically. Serum LFTs should be monitored more frequently in patients who develop elevations. Riluzole therapy was discontinued for LFT elevations >5× normal in ALS field trials. In the current study, one patient demonstrated an asymptomatic increase in ALT that exceeded nine times normal, but ALT quickly declined upon repeat testing and careful weekly monitoring. LFTs were monitored every third week in the current study and more frequently in those patients who developed significant elevations.

This study has several limitations, including its open-label design, relatively small number of patients, lack of a washout prior to initiation of riluzole and concomitant treatment with standard psychotropic medications. Use of concomitant medications makes it impossible to determine whether treatment response was due to riluzole alone or its combination with other medications. This study also does not address the long-term effects of treatment with riluzole. Finally, patients were required to have had stable medications regimens for only four weeks prior to study initiation, raising the possibility that some of the treatment effect represented a delayed response to the earlier initiation of other medications. Despite these limitations, the significant improvement in Y-BOCS scores in this treatment-resistant population suggests that riluzole addition may be of practical clinical benefit in patients with OCD. Moreover, riluzole's efficacy in the current study has important theoretical implications for the potential role of glutamatergic systems in treatment of anxiety and mood disorders. Future placebo-controlled studies in larger populations is warranted to follow-up on these promising preliminary findings.

Example 2

Use of Glutamate Modulating Agents for Treatment of Anxiety Disorders and Trichotillomania
Anxiety Disorders A study of thirteen patients with anxiety and mood symptoms was undertaken. Patients' baseline anxiety was measured using the Hamilton Anxiety Scale (HAM-A). The HAM-A is a rating scale developed to quantify the severity of anxiety symptomatology, often used in psychotropic drug evaluation. It consists of 14 items, each defined by a series of symptoms. Each item is rated on a 5-point scale, ranging from 0 (not present) to 4 (severe). Patients were then treated with Riluzole, a glutamate modulating agent, and HAM-D was followed weekly.

Methods. Thirteen patients between 18-65 years with anxiety symptoms were treated with the addition of riluzole to their existing pharmacotherapy. Hamilton Anxiety Inventory (HAM-A) scores were obtained weekly.

Figure 5:
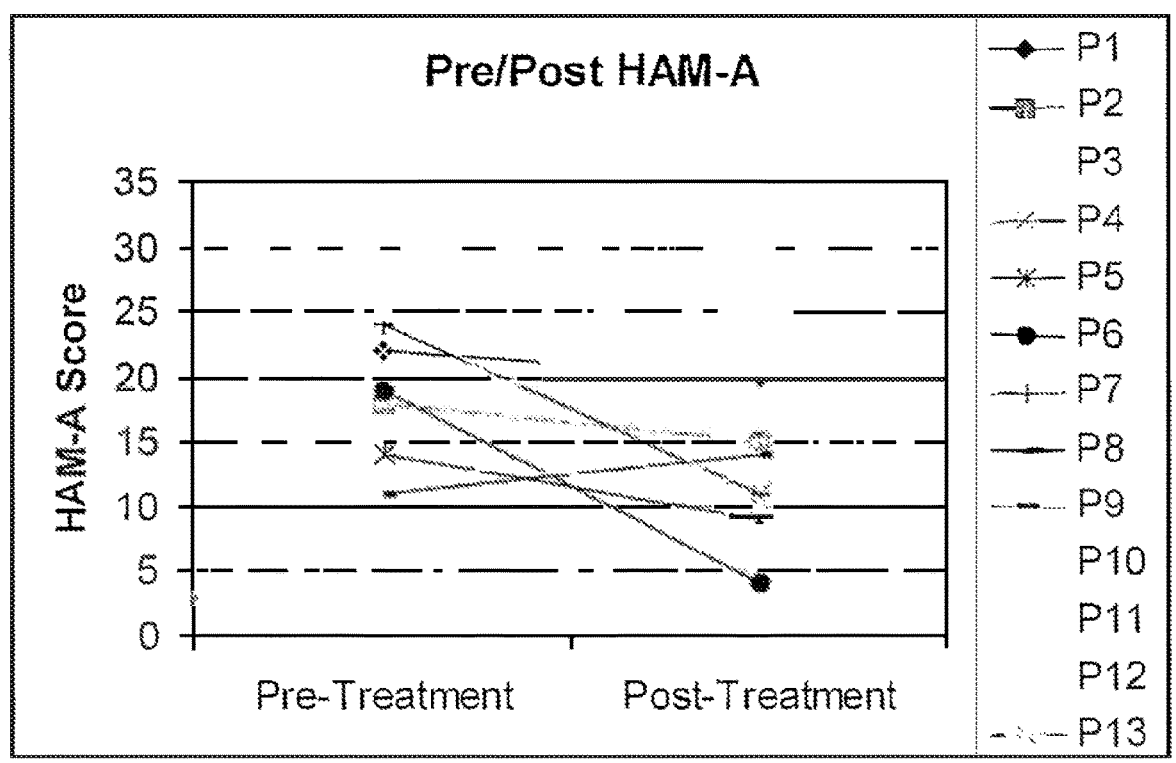
FIG. 5 shows pre- and post-treatment HAM-A scores for anxiety and mood symptoms patients treated with riluzole.
Figure 6:
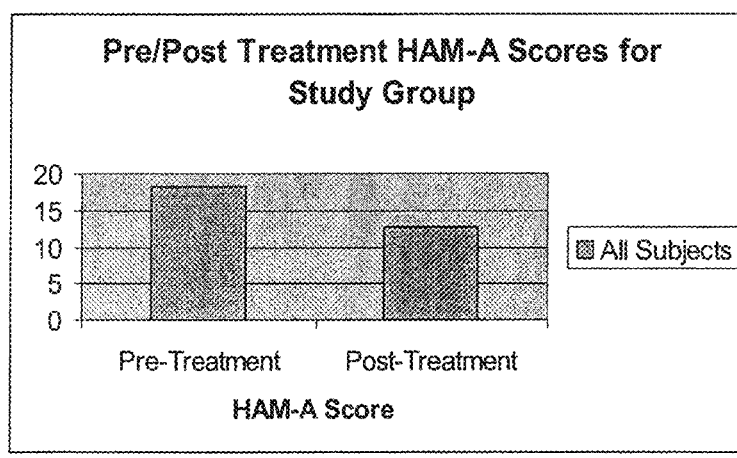
FIG. 6 shows mean pre- and post-treatment HAM-A scores for anxiety and mood symptoms patients treated with riluzole.

Results: Thirteen study participants received Riluzole 50 mg twice a day. HAM-A scores for the group significantly improved over time ($F_{1,10.8}=9.12$, $p=0.12$; $F_{1,11.2}=7.9$, $p=0.017$, respectively). Riluzole was well tolerated with no serious adverse effects noted. FIG. 5 shows pre- and post-treatment HAM-A scores for each study subject. Subjects P3, P5, P6, P7, P11, P12 with >1=35% reduction in HAM-A scores post study treatment with Riluzole. FIG. 6 shows mean pre- and post-treatment HAM-A scores for each study subject. Thirteen study participants received Riluzole 50 mg twice a day. HAM-A scores for the group significantly improved over time ($F_{1,10.8}=9.12$, $p=0.012$; $F_{1,11.2}=7.9$, $p=0.017$, respectively). Mean Pre-Treatment HAM-A=18.2+/−6.2 and Mean Post-Treatment HAM-A=12.8+/−7.2.

Figure 7:
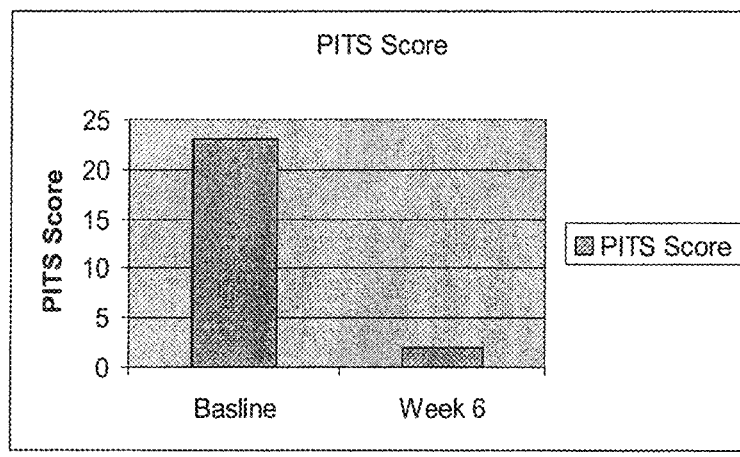
FIG. 7 shows pre- and post-riluzole treatment Massachusetts General Hospital (MGH) Hairpulling Scale and Psychiatric Institute Trichotillomania Scale (PITS) score for a patient treated with riluzole.
Figure 8:
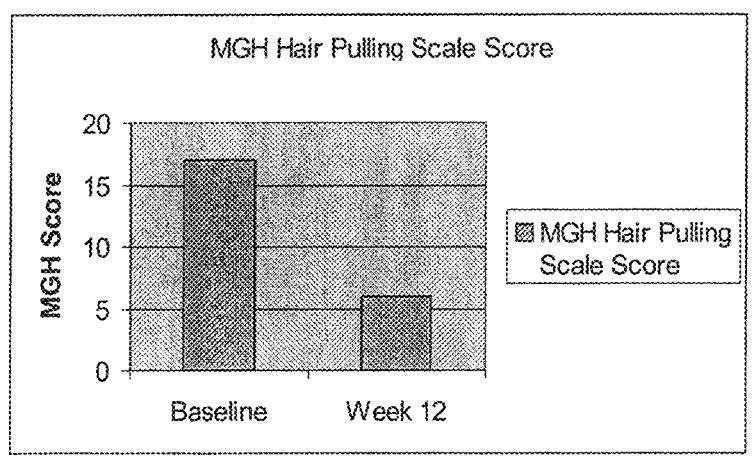
FIG. 8 shows pre- and post-riluzole treatment Massachusetts General Hospital (MGH) Hairpulling Scale score for a patient treated with riluzole.

Conclusions: Riluzole appears to have significant anxiolytic properties. Riluzole addition appears of practical clinical benefit in patients with anxiety symptoms.
Summary Taken together these findings demonstrate the usefulness of Riluzole and/or glutamate modulating agents as anxiolytic agents in the treatment of anxiety.
Trichotillomania Case Report: Mrs. Z is a woman with long history of Trichotillomania that failed to respond to prior treatment with serotonin reuptake inhibitor medications. She was being treated with Lexapro 30 mg and failed to demonstrate a treatment response. Treatment with riluzole was initiated at 50 mg twice a day and titrated to 100 mg twice a day. Mrs. Z demonstrated a marked reduction in Trichotillomania symptoms as evidence by clinically significant reductions in Massachusetts General Hospital (MGH) Hairpulling Scale and Psychiatric Institute Trichotillomania Scale (PITS). FIG. 7 shows a 74% Reduction in PITS score after 6 weeks of treatment with Riluzole addition. FIG. 8 shows pre- and post-riluzole treatment Massachusetts General Hospital (MGH) Hairpulling Scale score. There was a >35% Reduction in MGH Pulling Scale Score after 12 weeks of treatment with Riluzole. Mrs. Z experienced a cessation of Trichotollomania symptoms.
Summary This case report demonstrate the usefulness of Riluzole and/or glutamate modulating agents in the treatment of Trichotillomania.

Example 3

Beneficial Effects of the Antiglutamatergic Agent Riluzole in a Patient Diagnosed with Trichotillomania Trichotillomania (TTM) is an impulse-control disorder characterized by compulsive hair-pulling. While the incidence of hair-pulling is quite high in some populations, full criteria for TTM are met by less than 1% of the population (Christensen et al., *J. Clin. Psychiatry* 52(10):415-7, 1991; King et al., *J. Am. Acad. Child Adolesc. Psychiatry* 38(12): 1470-1, 1995; Walsh and McDougle, *Expert Opin. Pharmacother.* 6(6):975-84, 2005). Severe cases can lead to bald patches and marked social disability. Although TTM is categorized as an impulse-control disorder, some clinicians conceptualize TTM as being part of a spectrum of disorders characterized by compulsive behavior, including obsessive-compulsive disorder (OCD) and Tourette's syndrome. The hypothesis that TTM and OCD are etiologically related is largely based upon phenomenological similarity, high levels of comorbidity, and an increased prevalence of OCD in first-degree relatives of TTM probands. While the proposition that OCD and TTM are related disorders remains controversial, it has motivated trials of pharmacological strategies known to be effective in OCD in patients with TTM. SSRI treatment of TTM has shown inconsistent results: two double-blind placebo-controlled studies of fluoxetine have failed to show any consistent benefit (Streinchenwein et al., *Am. J. Psychiatry* 152: 1192-1196, 1995; Christenson et al., *Am. J. Psychiatry* 148:1566-1571, 1991; Stanley et al., *J. Clin. Psychiatry* 52:282, 1991; Stanley et al., *Psychopharmacol.* 17(4):278-83, 1997; reviewed in Walsh and McDougle, *Expert Opin. Pharmacother.* 6(6): 975-84, 2005); while clomipramine, a tricyclic antidepressant with strong serotonin reuptake inhibitory activity, has shown benefit in TTM in a few clinical studies, though in some studies most patients appear to relapse after weeks or months of continued treatment (e.g. Swedo et al., *N. Engl. J. Med.* 321(8):497-501, 1989; Swedo et al., *N. Engl. J. Med.* 329(2):141-2, 1993; reviewed in Walsh and McDougle, *Expert Opin. Pharmacother.* 6(6):975-84, 2005). Augmentation of SSRI treatment with atypical antipsychotics, which is effective in some cases of SSRI-resistant OCD, has shown a significant decrease in hair-pulling in some case reports and small open-label series (reviewed in Walsh and McDougle, *Expert Opin. Pharmacother.* 6(6):975-84, 2005).

Preclinical and clinical observations suggest that dysregulated glutamate activity may contribute to the pathophysiology OCD, and we have observed benefit from drugs that modulate glutamatergic neurotransmission in preliminary studies (Pittenger et al., *The Journal of the American Society for Experimental NeuroTherapeutics* 3:69-81, 2006). In particular, we found the antiglutamatergic drug riluzole (Rilutek, Aventis Pharmaceuticals), which is thought to reduce synaptic glutamate, to be of benefit to patients with refractory OCD in an initial open-label trial (Coric et al., *Psychopharmacology,* 167:219-220, 2003; Coric et al, *Biol.*

Psychiatry, 58:424-428, 2005). Here, we describe the successful use of riluzole in a patient with severe, chronic TTM.

Ms. B is a 53 year-old woman with a history of TTM and recurrent major depression dating to adolescence. Previous adequate treatment trials without lasting effects included: cognitive behavioral therapy with experienced clinicians, SSRIs (fluoxetine, fluvoxamine, citalopram, escitalopram) and other antidepressants (bupropion, clomipramine, venlafaxine). The longest period of abstinence for hair-pulling was a three-week period in the late 1980s during an early SSRI trial, but symptoms returned shortly thereafter. At the time of presentation to our clinic, Ms. B was taking escitalopram 30 mg daily without benefit to her hair-pulling or depressive symptoms, and she was able to go at most two days without pulling.

Figure 9:
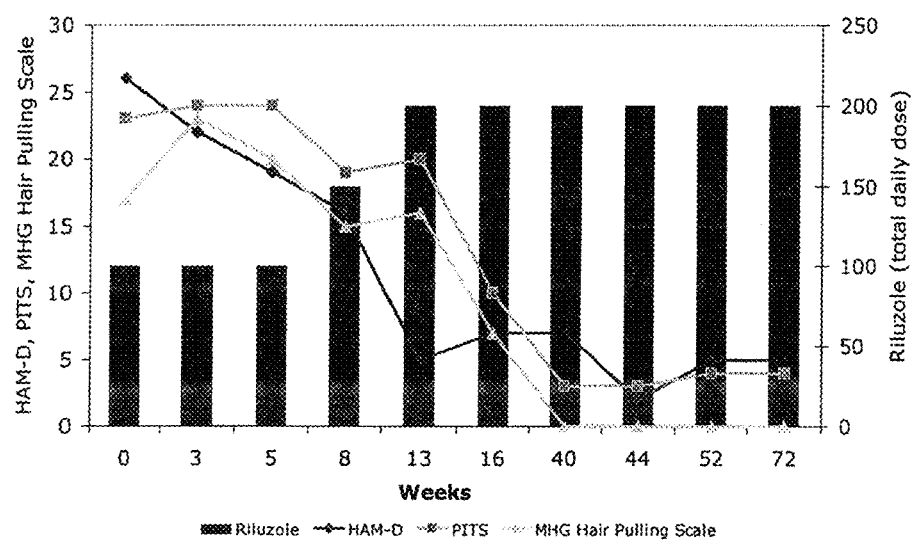
FIG. 9 shows the effects of riluzole in a patient diagnosed with trichotillomania.

The location of hair-pulling was mainly focused on the scalp, and she wore a hairpiece to cover her resultant frontal alopecia. Ms. B characterized her distress from hair-pulling as moderate to severe. Hair-pulling at presentation was severe, as quantified by a Psychiatric Institute Trichotillomania Scale (PITS) score of 23 and a Massachusetts General Hospital (MGH) Hairpulling Scale score of 17 (see FIG. 9). She also reported depressed mood, helplessness, hopelessness, decreased concentration, decreased interest in activities, low energy, insomnia, and feelings of extreme guilt and shame. Her Hamilton Depression Index (HAM-D) at presentation was 26.

After obtaining informed consent for off-label use, we initiated clinical treatment with riluzole at 50 mg twice a day. She experienced an initial decline in hair-pulling but then experienced a resurgence in symptoms. Over the course of three months, her riluzole was titrated upwards to 150 mg and then 200 mg daily to target her residual TTM and depressive symptoms. Depression improved rapidly, her HAM-D declined to 7 by week 16 (see FIG. 9). With up-titration of riluzole, her urges to pull vanished entirely, with a corresponding fall in her TTM ratings (see FIG. 9).

At recent follow-up (72 weeks after initiating riluzole treatment) Ms. B had continued on a stable dose of 100 mg twice a day of Riluzole and reported that urges to pull her hair continued to be minimal and readily ignored. Additionally, her improvement in mood persisted. Ms. B's decline in hair-pulling behaviors was also readily apparent by significant hair regrowth and continued reduction in TTM and depressive symptom rating scales (see FIG. 9). Her longtime outpatient clinician reported that Ms. B had previously been unable to maintain such an extended period free of significant hair-pulling, and found her to be more socially proactive and assertive, insightful, resilient to external stressors than at any time in the previous twenty years.

This case illustrates the potential utility of antiglutamatergic agents in the treatment of refractory trichotillomania. This mirrors the apparent utility previously reported in small studies and case series in OCD (Coric et al., *Psychopharmacology*, 167:219-220, 2003; Coric et al, *Biol. Psychiatry*, 58:424-428, 2005), compulsive skin picking (Sasso et al., *J. Clin. Psychopharmacolo.*, in press), and compulsive self-injurious behavior (Pittenger et al., *J. Clin. Psychiatry*. 66(11):1492-3, 2005). In addition, the improvement in her treatment-refractory depression adds to the growing literature on the utility of antiglutamatergic agents in the treatment of depression (e.g. Zarate et al., *Am. J. Psych.* 161: 171-4, 2004; Zarate et al., *Biol. Psych.* 57:430-432, 2005; Sanacora et al., *Ann. N.Y. Acad. Sci.* 1003:292-308, 2003; Sanacora et al., *Am. J. Psychiatry.* 161(11):2132, 2004). While the dramatic effect on her previously intractable TTM, in the context of previous studies suggesting a role for riluzole in the treatment of compulsive behavior syndromes, argues in favor of a direct effect of this glutamate modulating agent on her compulsive hair-pulling, it remains possible that the improvement of her TTM was secondary to the marked improvement in her depression (though historically in this patient TTM had persisted even during periods of improved mood). Although generalizations made from single case observations are inherently limited, our observations in this patient suggest that riluzole and other glutamate modulating agents merit further study in the treatment of refractory TTM.

Example 4

Beneficial Effects of the Glutamate Modulating Agent Riluzole on Disordered Eating and Pathological Skin Picking Behaviors Case Report Ms. B was a 52-year-old woman with a long history of disordered eating behaviors, pathological skin picking, obsessions, compulsions, depression, and a prior diagnosis of Attention-Deficit/Hyperactivity Disorder (ADHD). Diagnoses of OCD, Major Depressive Disorder (MDD), and Anorexia Nervosa were confirmed using the Structured Clinical Interview for DSM-IV Axis I Disorders-Clinician Version. Hasler et al., *Psychiatry Res.* 135(2):121-32, 2005. Her family history was significant for anorexia in her mother, bipolar disorder in her maternal grandmother, and alcoholism in her brother, father, and paternal grandfather.

Ms. B's disordered eating behaviors began in adolescence and had been present throughout adulthood. She alternated between periods of severe restricting, leading to multiple hospitalizations for failure to thrive, and periods of binging and purging. In the several-month period prior to admission, Ms. B would eat one small meal a day and purge "once on a good day, four times on a bad day." Ms. B also described longstanding skin picking behavior that was so severe that it led to recurrent facial infections requiring the care of a dermatologist and occasional antibiotic therapy. Any perceived flaw on her face would trigger the urge to scratch or squeeze the lesion, and she frequently used tweezers or pins for this purpose. She avoided social situations due to "shame" from the appearance of her excoriated facial skin. At the time of the initial interview, Ms. B had multiple lesions at different stages of healing over her face. Ms. B's OCD symptoms included severe hoarding, collecting, and organizing behaviors as well as obsessions surrounding hygiene and compulsive cleaning.

Ms. B had previously had trials of several antidepressants (selective serotonin reuptake inhibitors [SSRIs], paroxetine, fluoxetine, citalopram, nefazodone, and escitalopram; the serotonin/norepinephrine reuptake inhibitor duloxetine, and the tricyclic antidepressant clomipramine) alone or in combination with mood stabilizers (lithium and valproic acid) and antipsychotics (risperidone, ziprasidone, and aripiprazole). At the time of hospitalization, she had been on a stable regimen of fluoxetine 40 mg twice daily and amphetamine/dextroamphetamine 20 mg twice daily for two months.

Ms. B was admitted to the Clinical Neuroscience Research Unit of the Abraham Ribicoff Research Facilities (New Haven, Conn.). After providing informed consent for off-label medication use, riluzole 50 mg twice daily was added to her fluoxetine. Given the lack of prominent ADHD symptoms, amphetamine/dextroamphetamine was tapered and discontinued over three weeks. Riluzole was increased to 100 mg twice daily just prior to discharge to maximize symptom relief. Ms. B tolerated the riluzole well, complaining only of mild fatigue that resolved after the first several days of therapy. Liver enzymes were monitored monthly and remained stable. Ms. B participated in daily group and individual therapy, and a behavioral exposure and response prevention plan was instituted to target her obsessive ironing and cleaning behaviors. No specific behavioral interventions were directed at her eating or skin picking behaviors.

Eating behaviors were monitored by the patient's self-report and observations by treatment staff during meals. Weekly weights were not recorded, at the patient's request, due to extreme anxiety surrounding the notion of having her weight known. Ms. B's skin picking behaviors were also monitored by treatment staff, and she retrospectively reported the severity of these behaviors on the Skin Picking Impact Scale (SPIS), a 10-item validated self-report instrument designed to measure the psychosocial impact of repetitive skin picking. Keuthen et al., *Psychosomatics* 42(5):397-403, 2001. OCD and depressive symptoms were followed weekly with the Yale-Brown Obsessive-Compulsive Scale (Y-BOCS), the Hamilton Rating Scale for Anxiety (HAM-A), and the Hamilton Rating Scale for Depression (HAM-D.

Ms. B's symptoms improved significantly over the course of four weeks of riluzole augmentation. In regard to her disordered eating behavior, she initially struggled with menu selection, reported multiple false food allergies, and had difficulty eating in public at regularly scheduled meal times. By the end of her hospitalization, she described the following improvements: "I eat and don't obsess about it for hours. I'm okay eating at a table. I eat four times a day. I don't even get urges to vomit." During the second week of treatment, she purged twice in one day. Thereafter, she reported only a single urge to vomit, in week three, which she was able to suppress. Regarding her eating behavior overall, Ms. B reported on discharge, "Now, I feel like a regular person."

Figure 10A:
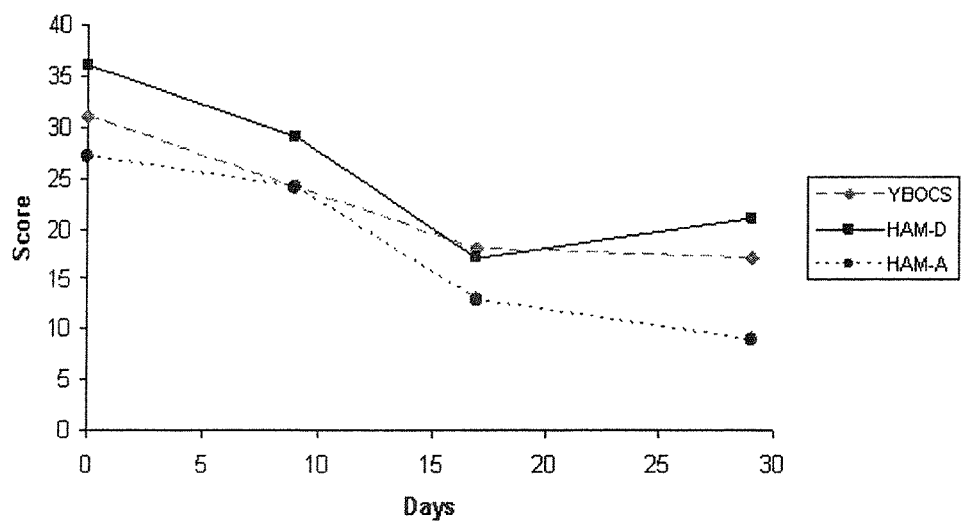
FIG. 10A shows YBOCS, HAM-D, and HAM-A scores for a patient over the first month of treatment with riluzole.
Figure 10B:
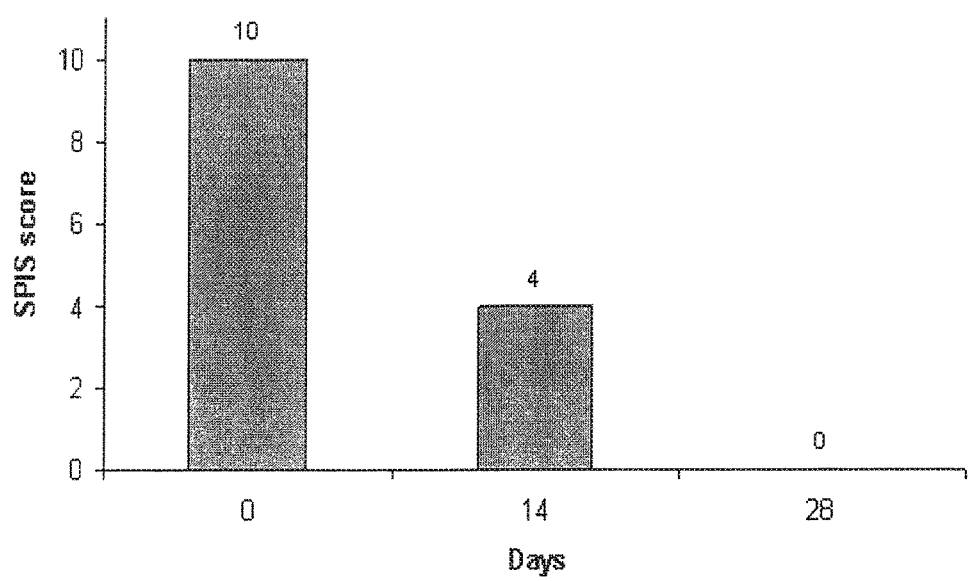
FIG. 10B shows Skin Picking Impact Scale (SPIS) scores for a patient over the first six weeks of treatment with riluzole, scored retrospectively by the patient's self-report.

Ms. B also noted significant improvement in her skin picking behaviors (see FIG. 10B). She stated that her urge to pick became less intense and that she no longer had to use make-up to cover facial lesions. Clinically, her skin looked healthier, with no obvious excoriated areas. On discharge, she reported that the skin picking behavior "is still there, but it's better." This subjective improvement was consistent with staff's observations of attenuated skin picking behaviors, noted improvements in her facial lesions during direct clinical examination, and comparison of admission/discharge photographs.

Ms. B's scores on the Y-BOCS, HAM-A, and HAM-D improved steadily over the course of treatment (see FIG. 10A). Her obsessions and compulsive behaviors decreased, and she was able to reduce the amount of time she spent cleaning, ironing, and organizing. On the day of discharge, regarding her OCD symptoms, she noted, "This is as close to normal as I've ever felt. I've never had so much peace in my head." Ms. B was discharged on riluzole 100 mg twice daily and fluoxetine 40 mg twice daily.

Discussion

These clinical observations suggest the efficacy of a glutamate-modulating agent in the treatment of disordered eating and pathological skin picking. Glutamate participates importantly in the regulation of feeding behavior. Burns and Ritter, *Pharmacol. Biochem. Behav.* 56(1):145-9, 1997; Zeni et al., *Pharmacol. Biochem. Behav.* 65(1):67-74, 2000; Georgescu et al., *Neurosci.* 25(11):2933-40, 2005. Substantial data implicates glutamate and GABA in hypothalamic control of feeding through modulation of neuropeptide Y and pro-opiomelancortin-containing neurons. Duva et al., *Neurosci. Res.* 52(1):95-106, 2005; Kiss et al., *Neuroreport* 8(17):3703-7, 1997; van den Pol, *Neuron* 40(6):1059-61, 2003. Clinical studies have previously suggested efficacy of glutamate antagonists in disordered eating behaviors. Mills et al., *Qjm.* 91(7):493-503. 1998; McElroy et al., *Am. J. Psychiatry* 160(2):255-61, 2003; DeBernardi et al., *Prog. Neuropsychopharmacol. Biol. Psychiatry* 29(2):339-41, 2005. The preclinical and clinical evidence for the effects seen here on pathological skin picking (PSP) behavior is less plentiful. Arnold and colleagues (*CNS Drugs* 15(5):351-9, 2001) have reviewed the literature for pharmacological approaches to PSP management, which includes two randomized controlled trials of fluoxetine (Simeon et al., *J. Clin. Psychiatry* 58(8):341-7, 1997; Bloch et al., *Psychosomatics* 42(4):314-9, 2001) in addition to several case reports and series.

It is unclear how antiglutametergic agents such as riluzole may treat disordered eating and PSP behavior. Glutamate-modulating agents may have a nonspecific benefit on compulsive behaviors in general. Riluzole may pharmacologically modulate the reward value of these compulsive behaviors. It is known that glutamate can affect activity in the mesolimbic dopaminergic system, which is critically involved in reward processing and motivated behaviors. Olds and Milner, *J. Comp. Physiol. Psychol.* 47(6):419-27, 1954. Taber and Fibiger demonstrated glutamate regulation of feeding-evoked dopamine release in the ventral tegmental area and nucleus accumbens in rats. *Neuroscience* 76(4): 1105-12, 1997. More recent animal studies have demonstrated the effects of glutamate antagonists on attenuating self-administration of nicotine (Paterson et al., *Psychopharmacology (Berl).* 167(3):257-64, 2003) and heroin (Xi and Stein, *Psychopharmacology (Berl).* 164(2):144-50, 2002).

The phenomenological theme of irresistible urge and tension that is relieved when a compulsive behavior is performed is common to OCD, purging behavior, PSP, and drug-seeking behavior. This suggests the involvement of dysregulated reward pathways. Modulation of the mesolimbic dopaminergic reward pathways by antiglutamatergic agents is a parsimonious explanation for riluzole's efficacy in all three domains of symptoms afflicting the patient described here.

Limitations of this study include those inherent to a single case report and the retrospective collection of the SPIS ratings. In addition, it is impossible to know whether the effects observed are attributable to the riluzole or to the beneficial effects of being in a structured hospitalized environment away from the stressors of home or to the behavioral interventions described above. However, the data presented here not only offer further support for the efficacy of riluzole in treatment-refractory OCD and depression, but supply preliminary evidence for the efficacy of antiglutamatergic agents in disordered eating and pathological skin picking behavior. These findings provide grounds for further exploration of these potential therapeutic avenues and raise new questions about glutamate's role in the neural circuitry underlying varied psychiatric symptomatology.

Example 5

N-Acetylcysteine Augmentation in Serotonin Reuptake Inhibitor Refractory Obsessive Compulsive Disorder Ms. A was a 58 year-old woman with a history of childhood onset OCD who presented with severe OCD symptoms consisting of contamination fears, intrusive ego-dystonic thoughts, hoarding behaviors, excessive hand washing and repetitive rituals performing her laundry. Her OCD significantly interfered with her ability to complete basic tasks of life (including basic housekeeping and maintaining a sanitary home environment), establish and maintain interpersonal relationships, and was accompanied by feelings of self-loathing and shame. She had been hospitalized five previous times secondary to her OCD symptoms; her last hospitalization was twelve years prior to the current admission. She reported having a stable but partial response to fluvoxamine, which she had been taking at a dose of 300 mg daily for the preceding twelve years. Previous medication trials of fluoxetine, clomipramine and alprazolam had failed, as had previous attempts at behavior modification. She also had a history of recurrent major depressive disorder that had been in remission for over twelve years. Her family history was notable for a mother with depression, a father with alcohol abuse, and an uncle who committed suicide. She was perimenopausal at the time of presentation and had a history of hyperlipidemia and borderline hypertension but was taking no medications besides fluvoxamine.

Mrs. A presented to our clinic seeking help for persistent and severe OCD symptoms. Diagnosis of OCD was confirmed using the Structured Clinical Interview for DSM-IV Axis I Disorders-Clinician Version. First et al., *Structured clinical interview for DSM-IV Axis I Disorders* (SCID-I Clinician Version), American Psychiatric Press, Inc., Washington, D C, 1997. After informed consent, Ms. A was admitted to the Clinical Neuroscience Research Unit of the Abraham Ribicoff Research Facilities (New Haven, Conn.) and treated clinically with an off-label use of NAC augmentation of fluvoxamine. OCD symptoms were followed using weekly Yale-Brown Obsessive-Compulsive Scale (Y-BOCS) ratings.

NAC (United States Pharmacia grade and in capsule form) was initiated at a starting dose of 600 mg PO daily and titrated upward to a total daily dose of 3 grams per day over 6 weeks. NAC was continued at the dose of 3 grams per day for an additional seven weeks. Fluvoxamine 300 mg was continued throughout the NAC treatment period. Ms. A remained on the inpatient unit throughout the treatment period and received supportive psychotherapy. She did not participate in a formal or manual-driven cognitive behavioral treatment plan. In fact, she was resistant to implementing behavioral interventions given the past failure of such interventions.

Laboratory studies performed prior to the initiation of NAC revealed only hyperlipidemia; routine lab monitoring over the course of her admission revealed no further abnormalities. Ms. A reported a few episodes of mild, brief right hand tingling and a single day of xerostomia, but no further side effects were noted.

Figure 11:
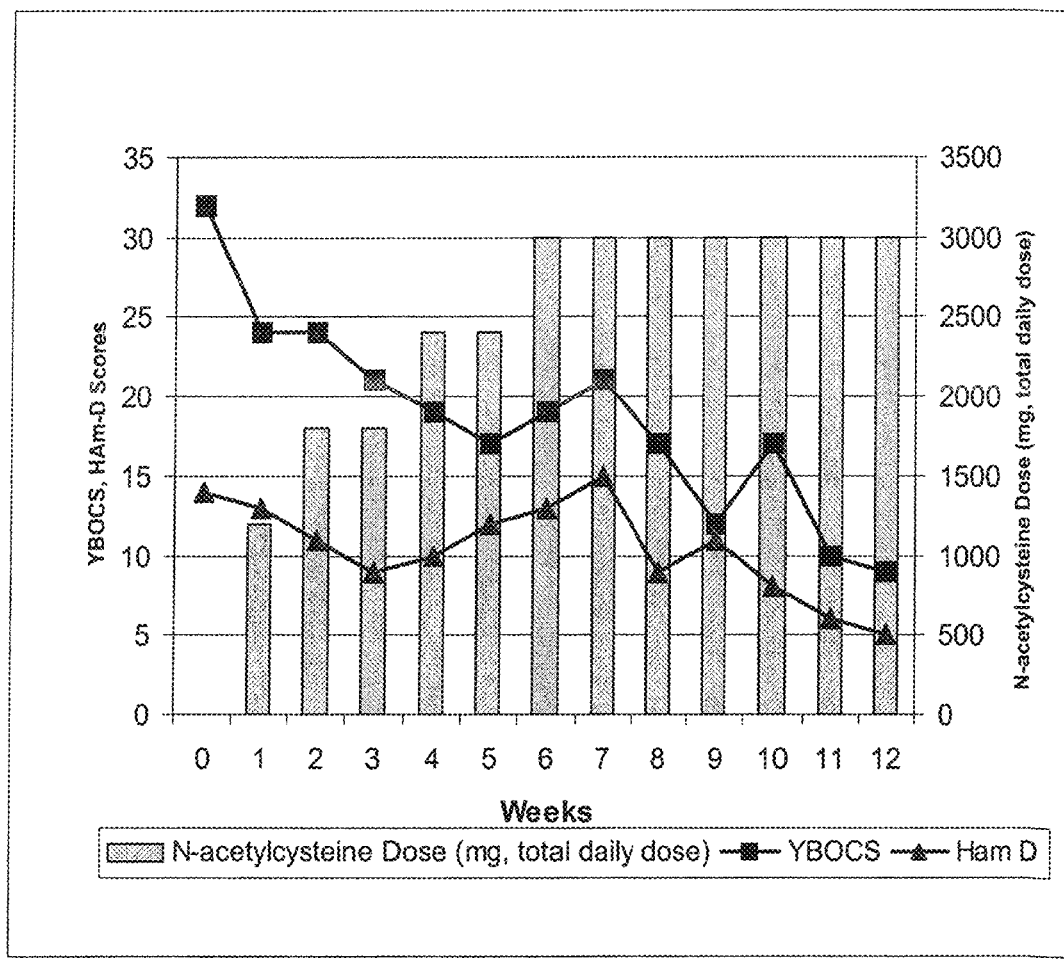
FIG. 11 shows the dose of NAC, Y-BOCS scores, and HAM-D scores in a patient with SRI-resistant OCD treated with fluvoxamine 300 mg and NAC 3 g (total daily doses).

Over the course of treatment with NAC augmentation, Ms. A's sense of contamination gradually decreased such that she began to be much less disturbed by intrusive thoughts of being contaminated. Y-BOCS score dramatically decreased with time (FIG. 11). She became better able to resist her compulsive washing rituals and was able to confront many obsessional triggers better than she had in many years. She was discharged home at the end of the trial with significantly improved symptoms and her symptoms remained improved at her two month follow-up visit (at the same dose of NAC and fluvoxamine).

Although caution is advisable in generalizing the findings of a single case, the response of this patient to NAC may be consistent with a hypothesized role for glutamatergic dysfunction as a contributing factor to OCD symptoms in patients who have not benefited from SRIs. However, the exact nature of the mechanism through which NAC might reduce OCD symptoms cannot be inferred from this case. As noted above, there are at least three general mechanisms through which NAC might work. Our primary hypothesis is that the benefits associated with NAC in this patient reflect that ability to reduce synaptic glutamatergic activity, perhaps via group II metabotropic glutamate receptors. If so, then group II metabotropic glutamate receptor agonists or positive allosteric modulators should also be explored as treatments for SRI-refractory OCD symptoms. The "glutamate release inhibition" hypothesis is consistent with evidence of glutamatergic hyperactivity in OCD and the preliminary report of the efficacy of riluzole, a drug that reduces glutamate release and stimulates glutamate uptake. Coric et al., *Biol. Psychiatry* 58:424-428, 2005. However, NAC also raises extrasynaptic glutamate levels and raises glutathione levels, and downstream consequences of these effects might have contributed to the current findings as well. The use of NAC in treatment-resistant OCD warrants further investigation, and may be advantageous over other glutamate modulating agents given its tolerability and low cost.

Example 6

Open-Label Study of Ceftriaxone Augmentation in SSRI-Refractory Obsessive Compulsive Disorder The primary objective of this study is to demonstrate the efficacy of ceftriaxone (Rocephin®) in the treatment of SSRI-refractory OCD. The reduction of OCD symptoms after two weeks of ceftriaxone therapy are measured by the Yale-Brown Obsessive-Compulsive Scale (Y-BOCS). Ceftriaxone is an FDA approved antibiotic medication and indicated for: lower respiratory tract infections, acute bacterial otitis media, skin and skin structure infections, urinary tract infections, uncomplicated gonorrhea, pelvic inflammatory disease, bacterial septicemia, bone/joint infections, intra-abdominal infections, surgical prophylaxis, and meningitis. Ceftriaxone was previously without psychiatric indications.

Glutamate Dysregulation in OCD: Preclinical and Clinical Studies.

A number of convergent lines of evidence support the notion that dysregulation of glutamate neurotransmission contributes to the pathophysiology of OCD. This perspective is independent of the monoaminergic hypotheses that underlie established treatments. There is reason to hope, therefore, that patients whose symptoms are relatively untouched by pharmacological therapies aimed at the monoaminergic systems may find relief in novel therapies aimed at normalizing glutamatergic neurotransmission.

Preclinical Evidence Suggesting Increased Glutamate Activity Worsens OCD-Like Behaviors.

A few rodent models of OCD and OCD-spectrum disorders have been developed. Joel, *Prog Neuropsychopharmacol Biol Psychiatry*, in press, 2006. In some cases, involvement of molecules or brain regions hypothesized to be involved in OCD, or response to SSRI medication, lends specific rodent models of OCD a degree of face validity. Current models are largely characterized by observable repetitive behaviors. In one such model, transgenic mice express a neuropotentiating subunit of the cholera toxin in dopamine D1 receptor-expressing limbic cortical cells. This is presumed to increase their firing rate in a way that may resemble the hyperactive limbic cortical areas seen in functional imaging of OCD patients; indeed, these transgenic mice are described as engaging in perseverative behaviors that mimic some aspects of OCD and Tourette's syndrome. MK-801, a non-competitive use-dependent antagonist of the NMDA glutamate receptor that indirectly increases presynaptic glutamate release (Moghaddam et al., *J. Neurosci.*

17:2921-7, 1997), has been shown to worsen these perseverative behaviors. Interestingly, NBQX, an antagonist of AMPA-type glutamate receptors, does not affect baseline OCD-like behaviors in these mice and does not attenuate the worsening of OCD-like behaviors induced by MK-801. While numerous caveats must attend any interpretation of results from a methodologically limited animal model of OCD, the exacerbation of OCD-like behaviors by glutamatergic agents in this study supports an important role for increased glutamatergic tone in the pathogenesis of obsessive-compulsive disorder, and with implications for its treatment.

Magnetic Resonance Spectroscopy (MRS) Measurements of Glutamate Dysfunction in OCD.

Magnetic resonance spectroscopy allows measurement of the concentration of certain small molecules in the brain and other tissues. It has come to be widely used in neurology as a tool to assess the health and cellular composition of different regions of the normal or diseased brain. The more recent development of methods to measure amino acid neurotransmitters in the brain has allowed levels of glutamatergic compounds and GABA to be investigated in neuropsychiatric disorders. Recent MRS findings implicate dysregulation of glutamate neurotransmission in corticostriatothalamocortical (CSTC) circuits in OCD. Rosenberg and colleagues have reported abnormal Glx measurements in several brain regions in OCD. *Int'l J. Neuropsychopharmacol.* 4(2):179-90, 2001. Glx is increased in the striatum of patients with OCD, consistent with the known metabolic hyperactivity of the CSTC circuitry. Interestingly, this elevation in Glx has been shown to normalize in OCD subjects who respond to treatment with SRI medications. In contrast, Rosenberg et al. found decreased Glx levels in the anterior cingulated in subjects with OCD. As these authors point out, the combined finding of reduced anterior cingulate Glx concentrations and increased caudate Glx parallels prior studies demonstrating an inverse relationship between anterior cingulate and basal ganglia volume in patients with OCD. The specific glutamatergic dysfunction in OCD remains to be elucidated and may vary between brain regions.

Elevated CSF Glutamate in OCD

The most direct evidence for excessive glutamatergic activity in OCD derives from a recent study examining cerebrospinal fluid (CSF) from patients with OCD. Chakrabarty et al. examined the CSF of 21 drug-naïve OCD patients and 18 control subjects, and found CSF glutamate levels to be significantly elevated in those subjects with OCD. *Neuropsychopharm.*, in press, 2006. This study requires replication with a larger number of patients, but it supports the MRS data in suggesting glutamatergic dysfunction as an important component of the pathophysiology of OCD.

Increased Cortical Excitability in OCD

Either increased glutamatergic tone or reduced GABA activity in the cortex may alter the excitatory-inhibitory balance in the cortex. This balance can be probed with transcranial magnetic stimulation (TMS), by measuring the motor response to a threshold cortical stimulation and other parameters. Using this methodology, Greenberg and colleagues recently demonstrated increased cortical excitability in OCD. *Neurology* 54:142-87, 2000. Future TMS studies are warranted to follow-up on this preliminary finding.

Genetics

OCD, like many psychiatric disorders, is complex and presumably polygenic. While OCD clearly has a heavy genetic loading, no clearly replicated genetic loci have been convincingly demonstrated to be causally involved in its pathogenesis. Nevertheless, several genes involved in glutamatergic neurotransmission have been implicated in single association studies. Delorme et al., *Neuroreport* 15:699-702, 2004. These include a preliminary association with the NMDA glutamate receptor subunit GRIN2B and a negative association with a particular allele of the GRIK2 kainate receptor gene. Such associations are very preliminary; but if these or similar genetic associations with components of the glutamate neurotransmission and regulatory systems are substantiated, they would bolster the evidence that dysregulated glutamate is an important aspect of the etiology of OCD.

The Use of Glutamate Modulating Agents has Beneficial Effects in Obsessive-Compulsive Disorder.

The availability of pharmaceutical agents that directly attenuate glutamatergic outflow via potent glutamate modulating agents has only recently become available. Riluzole (Rilutek; Aventis pharmaceuticals) is an antiglutamatergic agent that is FDA-approved for neuroprotection in amyotrophic lateral sclerosis. Without intending to be limited by theory, among the proposed mechanisms of action of riluzole are inhibition of sodium currents in glutamatergic (and other) axon terminals, reducing neurotransmitter release; reduction of P/Q-type calcium currents in the axon terminals, with a similar effect on transmitter release; extension of the open time of certain potassium channels and increased astrocytic uptake of glutamate. Although it has significant effects on glutamatergic function, riluzole is not a purely an antiglutamatergic agent. In vitro studies suggest that it also modulates release of acetylcholine and dopamine, potentiates receptors for GABA and glycine, and enhances expression of BDNF.

Riluzole therapy has been reported in several neuropsychiatric disorders in which excessive glutamatergic activity has been implicated. Case reports and open label studies have been reported in the treatment of major depression (Coric et al, *Biol. Psychiatry,* 58:424-428, 2005; Sanacora et al, *Am. J. Psychiatry,* 161:2132, 2004; Zarate et al., *Am. J. Psychiatry,* 161:171-174, 2004), bipolar depression (Zarate et al., *Biol. Psychiatry,* 57:430-432, 2005) anxiety (Coric et al, *Biol. Psychiatry,* 58:424-428, 2005), and OCD with major depression (Coric et al., *Psychopharmacology,* 167: 219-220, 2003; Coric et al, *Biol. Psychiatry,* 58:424-428, 2005).

These promising early results with riluzole encourage trials of other glutamate-modulating agents in OCD. An exciting new possibility is raised by a recent study revealing unexpected glutamate modulating properties of beta-lactam antibiotics. Rothstein and colleagues tested over 1,000 drugs in an in vitro assay and found that multiple beta-lactam compounds specifically upregulated the glial glutamate uptake transporter; tested beta-lactams proved to have neuroprotective effects in a mouse model of amyotrophic lateral sclerosis, demonstrating the physiological activity of the compounds. Rothstein et al., *Nature,* 433:73-77, 2005. Because of the extensive tolerability data on such compounds, they represent an exciting and unexpected group of potential antiglutamatergic agents for use in OCD and other neuropsychiatric disorders. Rothstein and colleagues demonstrated that ceftriaxone (Rocephin) upregulated the glial glutamate transporter more so than many other drugs. Also, their preclinical evidence suggests that beta-lactam antibiotics offer neuroprotection by selectively inducing transcription of the gene encoding the EAAT2 glutamate transporters, which are pumps that allow efficient recovery of released glutamate such that glutamate signaling is rapidly silenced, and prevent glutamate neurotoxicity. Rothstein et al., *Nature,* 433:73-77, 2005; Brown, *N. Engl. J. Med.,* 352:13, 2005. Ceftriaxone was shown to be neuroprotective when used in an animal model of Amyotrophic Lateral Sclerosis (ALS), ischemic injury, and motor neuron degeneration by increasing glutamate transport, as measured by L-[$^3$H] glutamate uptake into cortical membrane. See FIG. 3d of Rothstein et al., *Nature,* 433:73-77, 2005. Based on these findings, the development of clinical trials of ceftriaxone in subjects with ALS is underway. Brown, *N. Engl. J. Med.,* 352:13, 2005.

An Open-Label Study to Evaluate the Tolerability and Efficacy of Ceftriaxone (Rocephin) in the Treatment of Refractory OCD.

Overall Study Design

The efficacy of ceftriaxone treatment in SRI-refractory obsessive-compulsive disorder (OCD) is studied. Patients who meet the diagnostic criteria for OCD as stated in The Diagnostic and Statistical Manual of Mental Disorders, 4th edition-Text Revised (DSM-IV-TR) and have failed to respond to standard treatment with a serotonin reuptake inhibitor (SRI) are eligible.

Fifteen OCD patients are enrolled either as outpatients or inpatients depending on their clinical condition for a 4-week medication trial. Inpatients are admitted to the Clinical Neuroscience Research unit for the 4-week medication trial. The CNRU is a locked inpatient psychiatric unit devoted to clinical psychiatric research and is located on the third floor of the Connecticut Mental Health Center. The unit cares for individuals who are voluntarily admitted to try new treatments for their illnesses. Individuals admitted to the unit suffer from a variety of psychiatric illnesses. The CNRU houses, at most, thirteen research participants at any given time. Inpatient subjects are expected to remain inpatients for the entire four weeks of the study; however, patients routinely leave the unit three times a day for outside breaks and passes as warranted by their clinical condition. In an event that an inpatient subject decides to leave and wishes to continue the study as an outpatient, provisions are outlined to accommodate their preference. For example, as outpatient subjects, they are required to come in once a week for their weekly psychometric assessments and other tests. In the past studies, such accommodations have been granted even for out-of-town subjects. Visitors are allowed during scheduled visitation hours only. The inpatient setting may be required for the more severely ill population of patients who participate in this study. Individuals with refractory OCD who are willing to travel from other states for an opportunity to receive a novel treatment and inpatient care may participate in the study. Locally recruited subjects who meet inclusion criteria and desire an inpatient hospitalization are also be offered the opportunity for an inpatient admission if clinically indicated. After patients have provided informed consent and are screened for eligibility, they are enrolled in the trial.

Baseline assessments and basic laboratory work-up are performed on Days 1-3. Patients are continued on all their current medications unless contraindicated. On Day 4, all enrolled patients start the study trial with ceftriaxone 2 gm once a day. The dose of the study drug remains the same during the entire study. Experimental subjects receive weekly psychometric assessments.

Study Schedule

Screening and Initial Assessments (Day 1-3):

The screening evaluation includes an assessment of whether the patient qualifies based on inclusion/exclusion criteria (see below, Subject Population). In addition, the following assessments or procedures are completed at Day 1 to determine the subject's eligibility:

All Subjects:

Written informed consent (competency to provide consent is to be judged by the investigator). Whenever indicated, the patient's primary clinician, family and significant others will be involved in the consent process.

Demographic data; medical history; psychiatric history, including documentation of clinical diagnosis; and current medication usage Confirmation of diagnosis with Structured Clinical Interview for DSM-IV Axis I disorders (SCID-I)

Physical and neurological examination, including measurement of blood pressure, heart rate, weight and height Clinical laboratory tests including liver function tests, hematology, clinical chemistry, thyroid function tests.

Urine human chorionic gonadotrophin (HCG) pregnancy test (for all women) 12-lead ECG.

Prior medication history

Baseline Y-BOCS

Placement of PICC line

The Following Psychometric Assessments or Procedures are Conducted on Days 2-3:

CGI Severity of Illness item

Hamilton Rating Scale for Anxiety (HAM-A)

Hamilton Rating Scale for Depression (HAM-D)

Beck Depression Inventory (BDI)

Screen for tic disorders using the relevant portions of the Schedule for Tourette's Syndrome and Other Behavioral Syndromes for DSM-IV and the Yale Global Tic Severity Scale (rated from 0=none to 5=always) used to measure frequency of tics for those with tics.

Dysfunctional Attitude Survey (DAS)

Attributional Style Questionnaire (ASQ)

Social Adjustment Scale (SAS)

Treatment Phase (Days 4-14)

Subjects receive Ceftriaxone 2 gm thru a PICC (peripherally Inserted Central Catheter) line, once-a-day and remain at this dose for the four weeks of the study. Subjects will receive weekly psychometric assessments.

Routine serum chemistry, hematology are collected periodically as clinically indicated. Stool is analyzed for *Clostridium difficile* if subject experiences diarrhea for three consecutive days.

Outcome Measures

Assessments are performed as per the schedule of study procedures. The outcome measures include:

Primary Measure:

The mean difference from baseline Y-BOCS score at end of treatment (week 4).

Secondary Measures:

The proportion of patients who achieve reductions of 35% or greater from baseline Y-BOCS total score at weeks 1-12 or at withdrawal from the study.

The mean change in Clinical Global Impression score measured at the end of each week between medication and placebo groups The mean change in Hamilton Depression and Anxiety measured at the end of each week.

The mean change in Beck Depression scale measured at the end of each week.

The change in Yale Global Tic Severity Scale (if tics are present).

Other tolerability and safety measures will include the reporting of adverse events, clinically significant changes in the results of hematology and clinical chemistry tests (including liver function tests, thyroid function tests, serum glucose and lipid concentrations measured under fasting conditions), vital signs, and electrocardiogram results.

Subjects' symptomatology will be evaluated throughout the trial. After an initial inquiry, the subject will be asked, "Has anything bothered you since the last visit (or last assessment)?" Patients also will be instructed to volunteer AE's noted any time during the trial.

The following criteria are used to define treatment response: 35% or greater improvement on Y-BOCS from baseline and a final Y-BOCS of 16 or less.

a final CGI rating of "much improved" or "very much improved"

Consensus of the treating clinician and two of the primary investigators that the patient's condition was improved.

Study Medications

Ceftriaxone is obtained from the CMHC pharmacy. Trial medication is dosed at 2 gm and administered thru a PICC line, once a day, throughout the four week (28 day) treatment period.

All previously administered psychoactive medications, including benzodiazepine, anxiolytic, neuroleptic, antidepressant, and mood stabilizing medication, are continued throughout the study.

Concomitant Medications

Initiation of concomitant medication use during the trial is restricted as stated below.

Antidepressant, anxiolytic, neuroleptic and mood-stabilizing medication usage will be permitted only if it has been prescribed at least one month prior to Day 1 of the trial. Patients taking medication for sleep can continue to do so provided it is taken only at bedtime for sleep.

The use of potent cytochrome P450 inducers (including but not limited to carbamazepine, phenobarbital, and phenytoin) and inhibitors (including but not limited to ketoconazole, azole antifungals, erythromycin, macrolide antibiotics, and protease inhibitors) is not permitted within 14 days of baseline (Day 1) or during the randomized treatment period. Women who enter the trial with an intrauterine device in place, using oral contraceptives, or using injectable or implantable hormonal agents designed to prevent pregnancy may continue these treatments throughout the trial.

Use of other prescription and nonprescription medications must be agreed upon before each patient is enrolled. Acetaminophen (without caffeine) preparations are the only medications allowed for analgesia.

Subject Withdrawal

Patients may be withdrawn from the trial for any of the following reasons:

lack of efficacy (requiring alternative treatment)
adverse effects (including positive stool sampling for *Clostridium difficile*)
subject lost to follow-up (dropouts)
protocol noncompliance (protocol violations or deviations)
withdrawal of consent
at the investigator's discretion Any subject who withdraws during the trial and has clinically significant or abnormal findings on any safety assessment will have a follow-up visit within 1 week and at appropriate intervals thereafter until the abnormality resolves. Where possible, patients are followed up for 30 days after the last dose of trial drug is given.

Primary Analysis:

Y-BOCS scores in SRI-refractory OCD subjects decrease as a result of completion a 4-week course of Ceftriaxone treatment. All outcomes are summarized descriptively and assessed for normality prior to analysis using normal probability plots and Kolmogorov test statistics. Transformations or nonparametric analyses are performed as necessary. The primary outcome in this study is the Y-BOCS measured over time and is evaluated using linear mixed models where time (baseline, weeks 1-4) is included as a within-subject explanatory factor. The best fitting variance-covariance structure is chosen based on information criteria. Appropriate post-hoc comparisons is performed to compare levels between different time points. Secondary outcomes are evaluated using similar models.

Secondary Analyses:

HAM-D, HAM-A and CGI scores improve after Ceftriaxone augmentation. Paired t-tests or non-parametric equivalents are used for comparison of pre-versus post-treatment changes in these secondary outcome measures. Treatment response rates are estimated by proportion of subjects meeting criteria as defined in the Outcome Measures section. Exploratory repeated measures analyses with time as within-subject factor are performed on all outcome measures.

Sample Size Calculation:

In the above-described study examining the effects of riluzole in treatment-resistant OCD patients and using a similar protocol to the one proposed here, the effect size in the comparisons of Y-BOCS between baseline and week 4 was 0.86. Coric et al, *Biol. Psychiatry*, 58:424-428, 2005. With a sample size of 15, based on a 2-tailed, paired t-test and alpha=0.05, there is an 80% statistical power to detect an effect size of 0.78. Thus, there is ample power to detect smaller effects than those found previously in a similar protocol.

Human Subjects

Inclusion Criteria, Subjects with Primary Diagnosis of OCD:

1) Voluntary signed informed consent prior to the performance of any study specific procedures
2) Subjects with a DSM-IV diagnosis of OCD that has failed to fully respond to at least 8 weeks of treatment with a Serotonin Reuptake Inhibitor (failure to fully respond as defined by a Y-BOCS score of greater than 16 despite SRI treatment)
3) OCD symptoms at least of one year's duration and of least moderate severity on the Clinical Global Impression Scale (CGI).
4) Males or Females between ages 18-65 year old. For females only: The subject must be non-pregnant, non-breast feeding and using an effective form of birth control or the subject must be least one year post-menopausal; or the subject a) has a negative urine pregnancy test (Beta-HCG), and b) agrees to practice contraception throughout the study.

Exclusion Criteria, Subjects with Primary Diagnosis of OCD:

1) Diagnosis of a primary psychotic disorder.
2) Active illicit substance abuse/dependence in the last one month
3) Subjects who have had psychosurgery
4) Recent (<1 month) change in psychotropic medications
5) Presence of clinically significant somatic disease and/or medical problem that requires frequent changes in medication.
6) History of or current seizure disorder
7) Evidence of Substance Use Disorder (DSM-1V) within past 1 months or current illicit drug use.
8) Known to be HIV positive.
9) Subjects known to have a previous allergic reaction to ceftriaxone or an anaphylactic reaction to penicillin.

10) Women who are pregnant, breast feeding, or of childbearing potential (not sterile nor using acceptable birth control).

Fifteen subjects with SRI-refractory OCD are recruited for the study. Eligible subjects are over 18 years old, of either gender, and meet the inclusion and be without any exclusion criteria as described above.

Example 7

Figure 12:
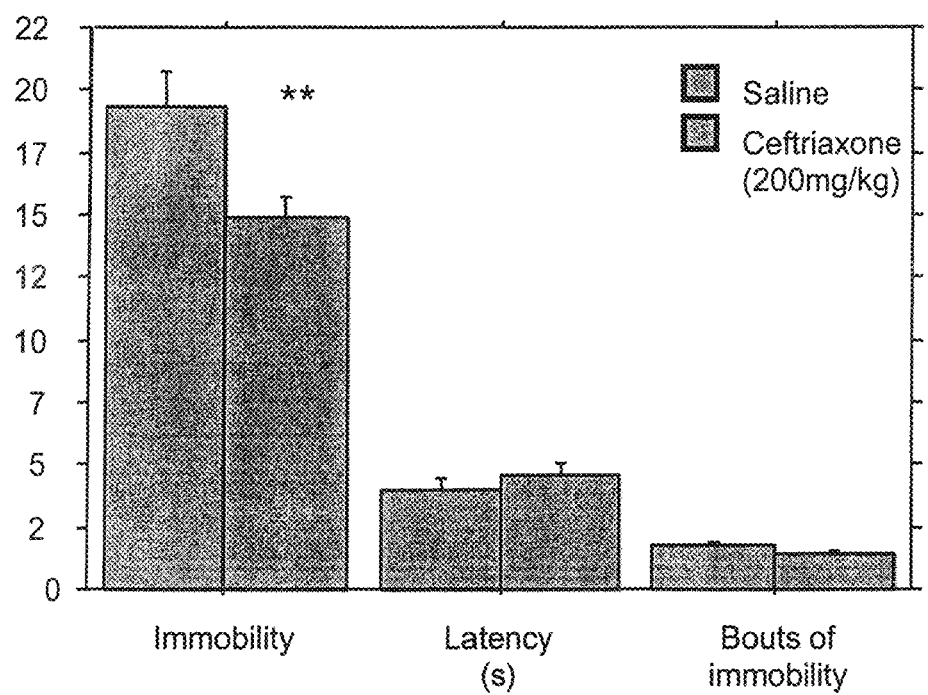
FIG. 12 shows the results of a tail suspension test in mice treated with ceftriaxone.

Tail Suspension Test 10 mice treated for 7 days with ceftriaxone and 10 mice treated with saline for 10 days were studied using the tail suspension test for antidepressant properties. The tail suspension test is a commonly used model to test antidepressant properties of novel drug compounds. As shown in FIG. 12 (after 7 days; 1 injection/day; C57BL/6J males; 10 animals/group; 16 weeks of age), there was nearly a 20% decrease in the immobility time (this percent reduction in immobility is consistent with the response observed with antidepressant medications) and a trend for increased latency and decreased bouts of immobility in the mice pretreated with ceftriaxone. Ceftriaxone is a beta-lactam antibiotic drug known to increase glutamate clearance through the altered expression and function of glutamate transporters. These results demonstrate that ceftriaxone has antidepressant properties and would be an effective treatment for depressive disorders and other psychiatric disorders involving altered glutamate function.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method of treating a mental disorder in an individual in need thereof comprising administering to said individual an effective amount of riluzole alone in pharmaceutical dosage form, wherein said mental disorder is post-traumatic stress disorder.

2. The method according to claim 1 wherein said riluzole is administered in oral dosage form.

* * * * *